(12) United States Patent
Richter et al.

(10) Patent No.: US 10,436,684 B2
(45) Date of Patent: Oct. 8, 2019

(54) FUNCTIONALIZED SUPPORT FOR ANALYTICAL SAMPLE PREPARATION

(71) Applicant: Agilent Technologies, Inc., Santa Clara, CA (US)

(72) Inventors: Bruce Richter, Wilmington, DE (US); Derick Lucas, Wilmington, DE (US); David Long, Glen Mills, PA (US); Limian Zhao, West Chester, PA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 15/269,647

(22) Filed: Sep. 19, 2016

(65) Prior Publication Data

US 2018/0080858 A1 Mar. 22, 2018

(51) Int. Cl.
| | | |
|---|---|---|
| *G01N 1/00* | (2006.01) | |
| *G01N 1/40* | (2006.01) | |
| *B01D 15/38* | (2006.01) | |
| *B01J 20/22* | (2006.01) | |
| *B01J 20/28* | (2006.01) | |
| *B01J 20/289* | (2006.01) | |
| *G01N 30/72* | (2006.01) | |
| *G01N 30/84* | (2006.01) | |

(52) U.S. Cl.
CPC ......... *G01N 1/405* (2013.01); *B01D 15/3823* (2013.01); *B01J 20/22* (2013.01); *B01J 20/289* (2013.01); *B01J 20/28016* (2013.01); *G01N 30/72* (2013.01); *G01N 30/84* (2013.01); *B01J 2220/46* (2013.01); *B01J 2220/54* (2013.01); *G01N 2030/8435* (2013.01)

(58) Field of Classification Search
CPC ...................................................... G01N 1/405
USPC ........................................................ 436/161
See application file for complete search history.

(56) References Cited

U.S. PATENT DOCUMENTS

| | | |
|---|---|---|
| 4,539,399 A | 9/1985 | Armstrong |
| 6,017,458 A | 1/2000 | Ng et al. |
| 2011/0129944 A1* | 6/2011 | Wang ............... B82Y 15/00 436/529 |
| 2013/0053588 A1 | 2/2013 | Iraneta et al. |

(Continued)

OTHER PUBLICATIONS

Lai et al. (Chirality 16:592-597 (2004)) (Year: 2004).*

(Continued)

*Primary Examiner* — Christine T Mui
*Assistant Examiner* — Emily R. Berkeley

(57) ABSTRACT

Aspects of the present disclosure include a solid phase sorbent for preparation of analytical samples. The solid phase sorbent includes particles that are surface modified with an α-cyclodextrin moiety. Also provided is a method of reducing matrix effects in an analytical sample. In some embodiments, the method includes contacting a sample comprising a matrix-interfering agent and an analyte with α-cyclodextrin modified particles to produce a contacted sample wherein the matrix-interfering agent binds to the α-cyclodextrin modified particles; separating the α-cyclodextrin modified particles from the contacted sample to produce a matrix-reduced composition; and detecting the analyte in the matrix-reduced composition. Systems for practicing the subject methods are provided that include the subject solid phase sorbent.

20 Claims, 12 Drawing Sheets

General Formula

Specific structures

(56) References Cited

U.S. PATENT DOCUMENTS

2015/0076340 A1 3/2015 Liang et al.

OTHER PUBLICATIONS

Fujimura et al. (Analytical Chemistry, vol. 55, No. 3, Mar. 1983) (Year: 1983).*

Kawaguchi et al. (Analytical Chemistry, vol. 55, No. 12, Oct. 1983) (Year: 1983).*

Tihamer Hargitai and Yoshio Okamoto, Journal of Liquid Chromatography, 16(4), 843-858 (1993) (Year: 1993).*

Aburatani et al. Optical Resolving Ability of 3,5-Dimethylphenylcarbamates of Oligosaccharides and Cyclodextrins. Bull. Chem. Soc. Jpn., 63, 3606-3610 (1990) (Year: 1990).*

U.S. Appl. No. 14/740,829, filed Jun. 16, 2015.

Belyakova et al., Nanoporous β-Cyclodextrin-Containing Silicas: Synthesis, Structure and Properties, Chemistry, Physics and Technology of Surface, 2014, 5(4): 386-395.

Ghanem et al., Immobilized β-cyclodextrin-Based Silica vs polymer monoliths for chiral nano liquid chromatographic separation of racemates, Talanta, 2015, 132: 301-314.

Guo et al., Cyclodextrin-functionalized silica nanoparticles with dendrimer-like spacers for enantioselective capillary electrochromatography, Electrophoresis 2014, 35: 3549-3555.

Haginaka et al., β-Cyclodextrin Bonded Silica for Direct Injection Analysis of Drug Enantiomers in Serum by Liquid Chromatography, Anal. Chem. 1990, 62: 997-1000.

Ponchel et al., Cyclodextrin silica-based materials: advanced characterizations and study of their complexing behavior by diffuse reflectance UV-Vis spectroscopy, Microporous and Mesoporous Materials 2004, 75: 261-272.

Shiraishi et al., Immobilization of β-Cyclodextrin on Silica Gel, Bull. Chem. Soc. Jpn. 1986, 59: 507-510.

Tazerouti et al., Enantiomeric Separation of Drugs and Herbicides on a β-Cyclodextrin-Bonded Stationary Phase, Chirality, 2002, 14: 59-66.

Muderwan, et al., Urea bonded cyclodextrin derivatives onto silica for chiral HPLC, J. Sep. Sci., vol. 29, 2006, 1849-1871.

WIPO, et al., International Search Report and Written Opinion dated Oct. 2, 2017, Application No. PCT/US2017/040437, 9 pages.

* cited by examiner

FUNCTIONALIZED SUPPORT FOR ANALYTICAL SAMPLE PREPARATION

INTRODUCTION

Analytical testing and quantitation methods suffer from interferences caused by contaminants in a sample matrix that can decrease or increase sensitivity to various analytes disproportionately to their abundance in the sample. For example, liquid chromatography-mass spectrometry/mass spectrometry (LC/MS-MS) is a commonly used method for drug metabolism studies; however, matrix effects can lead to significant analytical errors from decreased precision, selectivity and sensitivity. For example, phospholipids such as phosphatidylcholines interfere with analyte ionization in electrospray MS detection by reducing analyte sensitivity, commonly referred to as ion suppression or matrix effects.

The presence of contaminants can result in incomplete solvent extraction and hence underreporting of analyte concentrations, or can build up on analytical instrumentation, destroying sensitivity or resulting in downtime while cleaning procedures are instituted. For example, contaminants such as phospholipids have a tendency to build up on a reverse phase HPLC column during repeated analyses of precipitated plasma samples. Accumulated phospholipids can bleed off in subsequent injections, causing a drift in analyte sensitivity over the course of multiple injections. Removing the phospholipids requires extensive solvent washing to regenerate a column to proper condition. Numerous methods for removing contaminants in analytical samples are available, including liquid/liquid extraction (LLE), protein precipitation (PPT) and solid phase extraction (SPE).

QuEChERS is a streamlined method used by analytical chemists to examine analytes such as pesticide residues in food. The name is a portmanteau word formed from "Quick, Easy, Cheap, Effective, Rugged, and Safe". The QuEChERS method can be modified to ensure efficient extraction of pH dependent compounds (e.g. phenoxyalcanoic acids), to minimize degradation of susceptible compounds (e.g. base and acid labile pesticides), provide cleanup for co-extracted compounds from the sample matrix, and/or to expand the spectrum of matrices covered. The analyst homogenizes the sample (e.g. fruit, vegetables, botanicals, etc.) and performs a liquid-liquid extraction with in some cases acetonitrile and a high concentration of salts (e.g. $MgSO_4$, NaCl, ammonium acetate, etc.). The organic layer is then transferred for dispersive SPE cleanup or SPE cleanup followed by analysis.

Many sample preparation methods suffer from the potential for analyte losses and significant matrix effects during MS analysis. There are multiple sample components that can be involved in ion suppression, whose effects result in the collection of invalid data. Procedures that can remove both lipids and other agents causing matrix effects from an analytical sample prior to performance of analytical procedures are of interest.

SUMMARY

Aspects of the present disclosure include a solid phase sorbent for preparation of analytical samples. The solid phase sorbent includes particles that are surface modified with an α-cyclodextrin moiety. Also provided is a method of reducing matrix effects in an analytical sample. In some embodiments, the method includes contacting a sample comprising a matrix-interfering agent and an analyte with α-cyclodextrin modified particles to produce a contacted sample wherein the matrix-interfering agent binds to the α-cyclodextrin modified particles; separating the α-cyclodextrin modified particles from the contacted sample to produce a matrix-reduced composition; and detecting the analyte in the matrix-reduced composition. Systems for practicing the subject methods are provided that include the subject solid phase sorbent.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
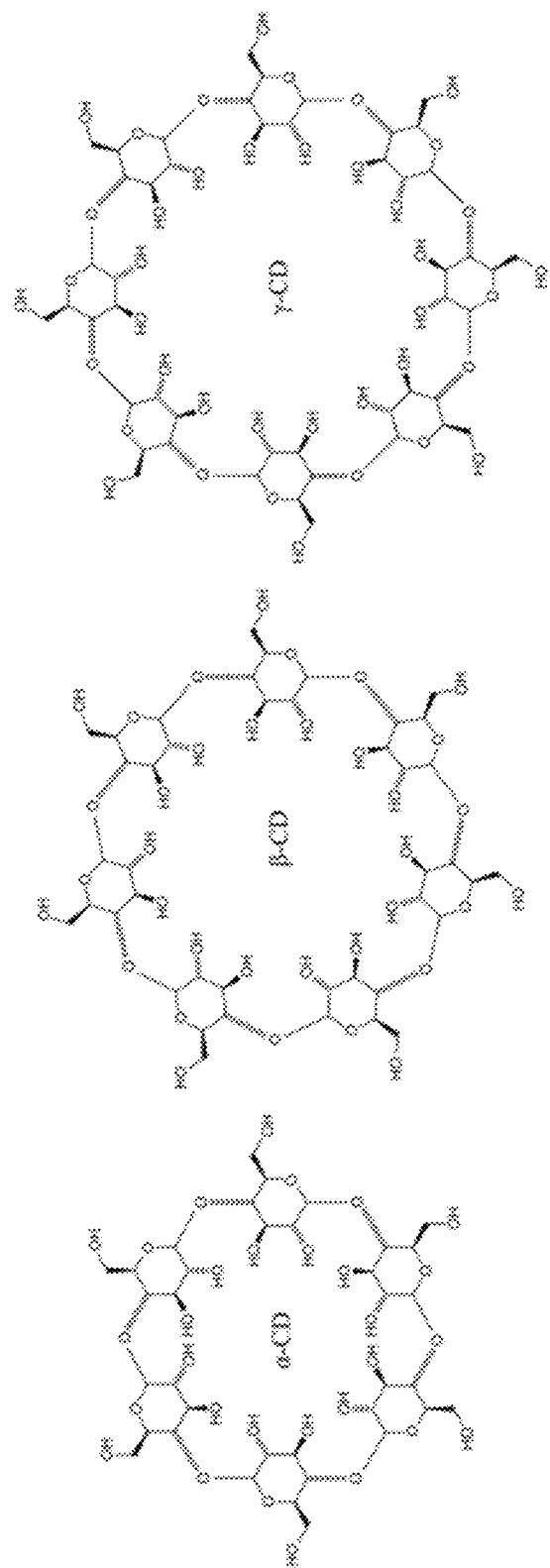
FIG. 1 shows chemical structures of α, β, and γ-cyclodextrin homologues.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "an α-cyclodextrin" refers to one or more α-cyclodextrins, i.e., a single α-cyclodextrin and multiple α-cyclodextrins. For example, the term "a particle" refers to one or more particles, i.e., a single particle and a plurality or particles in a composition. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "linker" or "linkage" refers to a linking moiety that connects two groups and has a backbone of 100 atoms or less in length, e.g., 20 atoms or less in length. A linker or linkage can be a covalent bond that connects two groups or a chain of between 1 and 100 atoms in length, for example of 1, 2, 3, 4, 5, 6, 8, 10, 12, 14, 16, 18 or 20 carbon atoms in length, where the linker can be linear, branched, cyclic or a single atom. In certain cases, one, two, three, four or five or more carbon atoms of a linker backbone can be optionally substituted with a sulfur, nitrogen or oxygen heteroatom. The bonds between backbone atoms can be saturated or unsaturated, usually not more than one, two, or three unsaturated bonds will be present in a linker backbone. The linker can include one or more substituent groups, for example with an alkyl, aryl or alkenyl group. A linker can include, without limitations, poly(ethylene glycol); ethers, thioethers, tertiary amines, alkyls, which can be straight or branched, e.g., methyl, ethyl, n-propyl, 1-methylethyl (iso-propyl), n-butyl, n-pentyl, 1,1-dimethylethyl (t-butyl), and the like. The linker backbone can include a cyclic group, for example, an aryl, a heterocycle or a cycloalkyl group, where 2 or more atoms, e.g., 2, 3 or 4 atoms, of the cyclic group are included in the backbone. A linker can be cleavable or non-cleavable.

As used herein, the term "specific binding member" refers to one member of a pair of molecules which have binding specificity for one another. One member of the pair of molecules can have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-1}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as, inter alia, $1 \times 10^{-9}$ M or less, $3 \times 10^{-10}$ M or less, $1 \times 10^{10}$ M or less, $3 \times 10^{-11}$ M or less, $1 \times 10^{-11}$ M or less, $3 \times 10^{-12}$ M or less or $1 \times 10^{-12}$ M or less.

The methods described herein include multiple steps. Each step can be performed after a predetermined amount of time has elapsed between steps, as desired. As such, the time between performing each step can be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step can be performed after an incubation or waiting time after completion of the previous step, e.g., a few minutes to an overnight waiting time.

A "plurality" contains at least 2 members. In certain cases, a plurality can have at least 6, at least 10, at least 12, at least 24, at least 48, at least 96, at least 100, at least 384, at least 10,000, at least 100,000, at least $10^6$, at least $10^7$, at least $10^8$ or at least $10^9$ or more members.

Numeric ranges are inclusive of the numbers defining the range.

The term "separating", as used herein, refers to physical separation of two elements (e.g., by size or affinity, etc.) as well as degradation of one element, leaving the other intact.

Components in a sample are termed "analytes" herein. In many embodiments, the sample is a complex sample containing at least about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $10^9$, $10^{10}$, $10^{11}$, $10^{12}$ or more species of analyte.

The term "analyte" are used herein interchangeably and refer to a known or unknown component of a sample. In some cases, analytes are biopolymers, i.e., an oligomer or polymer such as an oligonucleotide, a peptide, a polypeptide, an antibody, or the like. In some cases, an "analyte" is referenced as a moiety in a mobile phase (typically fluid), to be separated by chromatography using the subject particles.

The terms "derivatized" and "modified" refers to chemical modification of molecules. The skilled artisan would readily recognize the variety of ways molecules can be modified, such as oxidations, reductions, electrophilic/nucleophilic substitutions, alkylations, ester/amide formations and the like. For example, particles of the present disclosure can be chemically modified by silation.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH$_2$—), sec-butyl (($CH_3)(CH_3CH_2)$CH—), t-butyl (($CH_3)_3$C—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" can be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings can or can not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N—O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$- moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which can optionally include from 1 to 4 of the same or different additional heteroatoms selected from the group consisting of O, N and S, of which N can have —H or C$_1$-C$_3$ alkyl substitution; and each M$^+$ is a counter ion with a net single positive charge. Each M$^+$ can independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$ (M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the disclosure herein, in a certain embodiment, a group that is substituted has 1, 2, 3, or 4 substituents, 1, 2, or 3 substituents, 1 or 2 substituents, or 1 substituent. It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "polyisocyanate" refers to any di, tri, or other molecular species which incorporate two or more isocyanate functional groups. "R" represents the chemical product after attachment of the isocyanate species to the previously bonded aminosilane.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The terms "derivatized" and "derived from" refers to chemical modification of molecules. The skilled artisan would readily recognize the variety of ways molecules can be modified, such as oxidations, reductions, electrophilic/nucleophilic substitutions, alkylations, ester/amide formations and the like. For example, cyclodextrins of the present invention can be chemically modified by amination, tosylation, or iodination prior to polymerization or covalently attaching them to a polymer.

Other definitions of terms can appear throughout the specification.

DETAILED DESCRIPTION

As summarized above, aspects of the present disclosure include a solid phase sorbent for preparation of analytical samples. The solid phase sorbent includes particles that are surface modified with an α-cyclodextrin moiety. Also provided is a method of reducing matrix effects in an analytical sample. In some embodiments, the method includes contacting a sample comprising a matrix-interfering agent and an analyte with α-cyclodextrin modified particles to produce a contacted sample wherein the matrix-interfering agent binds to the α-cyclodextrin modified particles; separating the α-cyclodextrin modified particles from the contacted sample to produce a matrix-reduced composition; and detecting the analyte in the matrix-reduced composition. Systems for practicing the subject methods are provided that include the subject solid phase sorbent.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, compositions that find use in analytical sample treatment are described first in greater detail. Next, systems and kits of interest for including the subject compositions are reviewed. Finally, methods of reducing matrix effects in an analytical sample are also described.

Compositions

The present disclosure provides α-cyclodextrin (α-CD) functionalized solid phase supports which provide for rapid removal of sample components of interest (e.g., lipids) in any convenient separation method format. In some instances, the subject support finds use in a solid phase extraction (SPE) or a dispersive solid phase extraction (dSPE) procedure. The interactions between linear aliphatic compounds (e.g. lipids, surfactants) and α-CD are selective and can be exploited to separate such compounds from a sample of interest. In some embodiments, the sample is one which further includes a target analyte(s) of interest, in some cases, target trace analyte(s). When such a sample is contacted with the functionalized support, the trace analytes can pass through or remain unbound to the subject support, as target compounds are generally too physically or sterically large for complexation with the α-CD. The mechanisms and concepts of α-CD host-guest chemistry apply to the subject functionalized supports, where particular bonding and linking chemistries provide for attachment of α-cyclodextrin to a surface (e.g., a particle surface); allowing it to perform as a chromatography stationary phase for linear aliphatic compound (e.g. lipid) removal from an eluate. For example, when the support is a silica particle, a propyltriethyoxysilane linker can be utilized to functionalize the silica particle surface with α-CD molecules. A variety of other linkers and linker chemistries can also be utilized to attach the α-CD molecules to a support of interest, including branched linkers (e.g., trifunctional linkers) and divalent linkers (e.g., divalent linkers of 2-20 backbone atoms in length).

The α-CD-modified support offers matrix (e.g. lipid) removal in a variety of formats, such as a dSPE or a SPE tube format. Rigid particles can provide phase stability during SPE loading, pass-through, and elution. The functionalized α-CD particles remain insoluble in a variety of solvents and solvent mixtures and there are no observable morphological changes that hinder matrix removal or disrupt the eluent flow pattern (e.g. bed collapse, gelation, etc.). The insolubility of the subject modified supports prevents the introduction of soluble residues into the sample that may need to be removed prior to analysis. Therefore, in some cases, the subject supports eliminate the need for additional partitioning steps to remove contaminants prior to analysis (e.g., LC-MS).

The SPE format allows for retention or concentration of lipids/matrix on a stationary phase composed of a α-CD-modified support. The αCD-modified support is also compatible with a variety of organic solvents, such as acetonitrile, acetone, alcohols, as well as other water immiscible solvents. Trapped lipids/matrix that bind to the support can be subsequently eluted using a suitable eluent (e.g. hexane, dichloromethane, etc.).

The selectivity of the α-CD-modified supports generally provides for analytes to pass through without significant retention, providing for high analyte recoveries at low concentration in complex samples (e.g. avocado). Nonselective (secondary) interactions are minimized by utilizing a particular linking groups that does not interact with analytes of interest.

Synthesis of the αCD-modified support materials is inexpensive, simple, and effective for generating a support with high α-CD content (e.g., 30 wt % or less, such as up to 28 wt % or less or 22 wt % or less in silica particles). αCD-linker derivatives can be chemically deposited on a suitable particle (amorphous or spherical), membrane, or any other convenient solid support. The subject methods of preparation provide for other form factors and applications where selective lipid binding and entrapment is of interest.

As used herein, the terms "α-cyclodextrin", "α-dextrin", "alpha-cyclodextrin", "α-CD" and "alphadextrin" are used interchangeably and refer to a cyclic polysaccharide including six glucose subunits that are cyclically linked via α-1,4 intersubunit linkages. The term can be used in the context of a single monomeric compound, e.g., a compound that includes one α-cyclodextrin. The term can also be used in the context of a polymer, e.g., a co-polymer that includes α-cyclodextrin co-monomers. The term can be used to refer to monomeric α-cyclodextrin compounds or to α-cyclodextrin co-polymers. The glucose subunits of the α-cyclodextrin moieties can be naturally occurring sugars, in their reduced or oxidized forms. In some instances, the glucose subunits of the α-cyclodextrin are α-D-glucopyranoside units. The α-cyclodextrin moieties can be modified. A modified α-cyclodextrin is a moiety (e.g., a monomer or co-polymer) that includes at least one modified glucose subunit. Modifications of interest include, but are not limited to, modification at a 2-, 3- and/or 6-hydroxyl groups of a glucose unit (e.g., alkylation or acylation with any convenient linking moiety), substitution or transformation of a hydroxyl group (e.g., a 2-, 3- and/or 6-hydroxyl group) with an alternative functional group (e.g., an amine, a thiol, an aldehyde, a ketone, an azide, a carboxylic acid, an active ester, an isocyanate, an isothiocyanate, etc). α-Cyclodextrin moieties can include an optional linker for attachment to a co-polymer or other moiety of interest. The linkage can be covalent (e.g., via biohydrolyzable bonds, e.g., esters, amides, carbamates, and carbonates). α-Cyclodextrin moieties can further include one or more carbohydrate moieties, in some cases, simple carbohydrate moieties such as galactose, attached to the cyclic core, either directly (i.e., via a carbohydrate linkage) or through a linker group. The glucose subunits of the α-cyclodextrin can be the same or different. In some cases, one or more of the glucose subunits is modified to provide for covalent linking of the α-cyclodextrin to a moiety of interest.

The selectivity of the α-cyclodextrin moiety can be derived from a particular cavity size which restricts formation of inclusion complexes (i.e., a host-guest complex) to only those guest components able to be incorporated within the cavity of the α-cyclodextrin. Cavity size is a major determinant as to which components of the sample can be complexed. α-Cyclodextrins have small cavities (e.g., having an internal diameter of about 4.7 to about 5.3 angstroms relative to β- or γ-cyclodextrins, which have internal diameters of 6.0 to 6.5 angstroms and 7.5 to 8.3 angstroms, respectively) that are not capable of accepting molecules or groups having a larger size. The spatial fit of the component which binds in the α-cyclodextrin cavity is important to achieving complex formation.

As such, sample components that are too large to be included inside the α-cyclodextrin cavity remain unbound in solution. Cyclodextrins incorporate hydrophilic external surfaces and apolar internal cavities. The hydrophilic properties of the CD exterior allow it to dissolve in water as well as a variety of polar organic solvents. Inclusion complexes, form due to non-covalent hydrophobic and Van der Walls interactions between a potential guest molecule and the hydrophobic interior cavity of the cyclodextrin. Secondary interactions that promote the host-guest complex include hydrogen bonding and dipole-dipole interactions. α-CD, due to its smaller internal diameter, is able to readily complex linear alkyl chains while excluding larger molecules, and allows for its use in lipid removal from complex sample extracts while leaving behind the larger more complex compounds of interest in solution for detection and quantitation.

For example, in some cases, the sample includes a guest component of interest that is a lipid. Lipids have an extensive and complex role in biology and are found in the matrix of many types of samples. A lipid has a hydrophilic head group and a hydrophobic tail that includes a hydrocarbon chain. The hydrophobic tail of a lipid can have a linear extended structure that is cylindrical, i.e., a structure having a generally consistent diameter and a variable length determined by the length of the hydrocarbon chain. A lipid hydrocarbon chain can have any one of a variety of combination of lengths, substitution patterns, and degrees of unsaturation. Lipids have physical properties such as shape, rigidity and size. Membrane lipids can be classified according to their molecular shape: e.g., inverted cone, cylindrical and cone, which can determine membrane structure and biological function. Cylindrical shaped lipids are lipids whose hydrophilic head group and hydrophobic tail have similar diameters. Inverted cone shaped lipids are those in which the polar head group is greater in diameter than the lipid tail. Cone shaped lipids are those in which the polar head group is smaller in diameter than the lipid tail. In general terms, the hydrocarbon chains of lipids have an average diameter and shape that is capable of incorporation into the cavity of an α-cyclodextrin moiety. In some cases, depending of the length of the hydrocarbon chain, the hydrocarbon chain can form a host-guest complex with multiple α-cyclodextrin moieties simultaneously (e.g., multiple α-cyclodextrin moieties attached to a support). Lipids of interest that can be capable of forming complexes with the subject α-cyclodextrin compositions include, but are not limited to sphingolipids, glycophospholipids, acylglycerides and cholesterols.

In general terms, the subject supports include an α-cyclodextrin moiety that can selectively bind a target component of a sample of interest to produce a complex. As such, in some cases, the sample component can have an extended linear structure which is incorporated within, and projects through, the cavities of multiple α-cyclodextrin moieties. Once the complex is formed it can then be separated from the sample using any convenient method.

In some cases, the target component is a target analyte and the formation of a complex using a subject support provides for separation of the analyte from the contacted sample. Once the complex has been separated from the contacted sample, the target analyte can be subsequently detected and analyzed.

In certain cases, the target component is a sample component (e.g., a matrix interfering agent) whose presence interferes with the sensitive downstream detection and/or analysis of a target analyte. In such cases, the complex that is formed can be removed from the sample, and can provide for sensitive detection and analysis of a target analyte remaining in the sample.

α-Cyclodextrin compounds of interest that find use in functionalization of the subject supports include, but are not limited to, α-cyclodextrin, methyl-α-cyclodextrin, (2-hydroxypropyl)-α-cyclodextrin. In some embodiments, the α-cyclodextrin has the following structure:

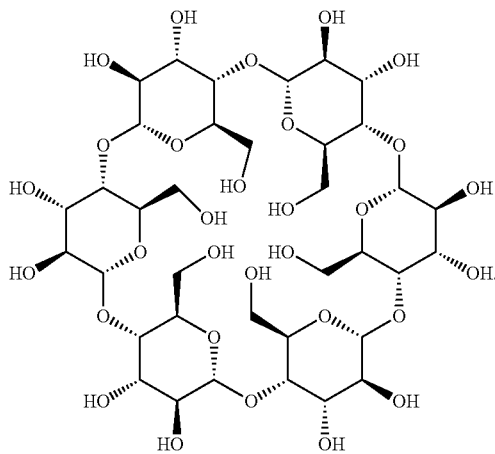 [SMILES: OC[C@H]1O[C@@H]2O[C@H]3[C@@H](O)[C@H](O)[C@@H](O[C@H]4[C@@H](O)[C@H](O)[C@@H](O[C@H]5[C@@H](O)[C@H](O)[C@@H](O[C@H]6[C@@H](O)[C@H](O)[C@@H](O[C@H]7[C@@H](O)[C@H](O)[C@@H](O[C@H]1[C@@H](O)[C@@H]2O)O[C@@H]7CO)O[C@@H]6CO)O[C@@H]5CO)O[C@@H]4CO)O[C@@H]3CO]

As used herein, in the subject functionalized supports, the following structure:

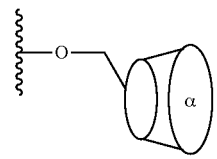

refers to both a 6-O-linked α-cyclodextrin including naturally occurring sugars and a 6-O-linked modified α-cyclodextrin. Any of the supports described herein can be functionalized with a 6-O-linked α-cyclodextrin moiety, via any convenient linker, e.g., any particular linker described herein. The α-cyclodextrin or α-cyclodextrin moiety can be linked to the support via any convenient functional groups of the molecule. In some cases, the α-cyclodextrin or α-cyclodextrin moiety is linked to the support via a hydroxyl group of the molecule. In certain instances, a variety of different hydroxyl group linkages to α-cyclodextrin or α-cyclodextrin moieties are present in a solid phase sorbent composition. In certain cases, the support is surface modified with one or more α-cyclodextrin or α-cyclodextrin moiety wherein each one or more α-cyclodextrin or α-cyclodextrin moiety can be linked to the support via a variety of hydroxyl groups, e.g., a 6-O linkage, a 3-O linkage and/or a 2-O linkage. For example, when an isocyanate (—NCO) chemistry is used for linking, in some case, the subject methods can provide for coupling reactions at all the different hydroxyls present on α-CD. In certain cases, coupling can be performed primarily at the hydroxyl groups in the 6-position. In certain cases, coupling can provide a distribution of linked α-CDs which are bound through the 6-OH, 3-OH, and/or the 2-OH groups of the α-CD.

In some embodiments, the subject support (e.g., particles) is functionalized (e.g., surface modified particles) with a α-cyclodextrin moiety that is a 6-hydroxyl-linked α-cyclodextrin. In certain embodiments, the subject support (e.g., particles) is functionalized (e.g., surface modified particles) with a α-cyclodextrin moiety that is a modified α-cyclodextrin (e.g., as described herein).

As used here, the term "functionalized" in the context of a support, refers to a support that has been chemically modified to include a group or moiety of interest that provides for a desirable physical and/or chemical property. A functionalized support is meant to include a support that has been chemically modified or derivatized such that inherent groups of the support are modified to produce a new and distinct functionality or chemical group. Depending on the support, inherent groups present, and chemistry used, a modified support can include such modifications at the surface, and/or within a porous structure of the support. In certain cases, modifications across the surface of a support can form a layer, e.g., a layer of a covalently attached molecule of interest. In some cases, the support can be derivatized with a linker (e.g., as described herein), which can find use in covalent attachment of a molecule of interest to the support. In such cases, the molecule of interest can be referred to as being linked to the support.

α-Cyclodextrin Polymers

In some instances, the subject supports are functionalized with an α-cyclodextrin co-polymer. As used herein, the term α-cyclodextrin co-polymer refers to a co-polymer having two or more distinct co-monomers, where at least one of the co-monomers is an α-cyclodextrin co-monomer, i.e., a co-monomer that includes an α-cyclodextrin compound, optionally modified, that is suitable for incorporation into the co-polymer. The α-cyclodextrin co-monomers present in the co-polymer define a series repeating α-cyclodextrin groups, which can be included as sidechain groups or can be included as an integral part of the polymeric backbone. The cyclodextrin co-polymer can include α-cyclodextrin co-monomers that are branched. A branched α-cyclodextrin co-monomer includes three or more linking moieties that provide for connection of the co-monomer to three other co-monomer subunits. In such cases, the co-polymer can be dendritic, i.e., have a dendrimer structure. In some instances, the α-cyclodextrin co-polymer includes 6 or less α-cyclodextrin monomeric units, such as 5 or less, 4 or less, 3 or less, or 2 units.

The cyclodextrin co-polymer can include α-cyclodextrin co-monomers that are functionalized. By functionalized is meant, the α-cyclodextrin co-monomer has been modified to include a group or moiety of interest that provides for a desirable physical or chemical property, such as a specific binding moiety, a water soluble group (WSG), or a detectable moiety (e.g., a fluorophore).

Any convenient polymer chemistries, linkages and co-monomers can be utilized in the preparation of the subject α-cyclodextrin co-polymer. The subject polymers can be prepared via polymerizations that can include radical, anionic, and cationic mechanisms, metal-catalyzed polymerizations such as olefin metathesis, other polymerization reactions known to those of skill in the art, as well as reactions of bifunctional molecules (analogous to the formation of nylon, e.g., reacting molecules each of which bears two or more different reactive moieties that react with each other, but, in some cases, are disfavored from reacting intramolecularly by steric, conformational, or other constraints, or reacting two or more different compounds, each compound bearing two or more reactive moieties that react only with reactive moieties of different compounds, i.e., intermolecularly). Polymer backbone linkages of interest that can be utilized in connecting the co-monomers of the co-polymer include, but are not limited to carbamate, vinyl, ether, acrylate, methacrylate, amide, aramid, ester, urethane, and carbonate. As such, in some cases, the α-cyclodextrin co-polymer can be referred to as a polycarbamate, a polyurethane, a polyacrylate, a polyamide, a polyester, or a polycarbonate, etc. In certain embodiments, the α-cyclodextrin co-polymer is a polyurethane polymer. In some cases, the α-cyclodextrin_co-polymer further includes a β-cyclodextrin or a γ-cyclodextrin co-monomer, where the β-cyclodextrin or a γ-cyclodextrin can be included as a sidechain group or integral to the polymeric backbone.

Any convenient co-monomers can be utilized in the co-polymer in addition to the α-cyclodextrin_co-monomer. As used herein, the term "co-monomer precursor" refers to any straight chain or branched, symmetric or asymmetric compound which upon reaction with an α-cyclodextrin monomer precursor links two such moieties together. In certain embodiments, a co-monomer precursor is a compound containing at least two functional groups through which reaction and thus linkage of the α-cyclodextrin co-monomers can be achieved. Examples of functional groups, which can be the same or different, terminal or internal, of each co-monomer precursor include, but are not limited to, amino, acid, imidazole, hydroxyl, thio, acyl halide, —C═C—, or —CC— groups and derivatives thereof. In some embodiments, the two functional groups are the same and are located at termini of the co-monomer precursor. In certain embodiments, a co-monomer precursor contains one or more pendant groups with at least one functional group through which reaction and thus linkage of a moiety of interest can be achieved, or branched polymerization can be achieved. Examples of functional groups, which can be the same or different, terminal or internal, of each co-monomer precursor pendant group include, but are not limited, to amino, acid, imidazole, hydroxyl, thiol, acyl halide, ethylene, ethyne, isocyanate and isothiocyanate groups and derivatives thereof. In certain embodiments, the pendant group is a (un)substituted branched, cyclic or straight chain C1-C10 (in some cases C1-C6) alkyl, or arylalkyl optionally containing one or more heteroatoms, e.g., N, O, S, within the chain or ring.

Upon copolymerization of a co-monomer precursor with an α-cyclodextrin monomer precursor, two α-cyclodextrin monomers can be linked together by joining the primary hydroxyl side of one α-cyclodextrin monomer with the primary hydroxyl side of another α-cyclodextrin monomer, by joining the secondary hydroxyl side of one α-cyclodextrin monomer with the secondary hydroxyl side of another α-cyclodextrin monomer, or by joining the primary hydroxyl side of one α-cyclodextrin monomer with the secondary hydroxyl side of another α-cyclodextrin monomer. Accordingly, combinations of such linkages can exist in the final copolymer. Both the co-monomer precursor and the resulting co-monomer of the final copolymer can be neutral, cationic (e.g., by containing protonated groups such as, for example, quaternary ammonium groups), or anionic (e.g., by containing deprotonated groups, such as, for example, sulfate, phosphate, borinate or carboxylate).

In some embodiments, the co-polymer includes a co-monomer derived from a diol or a triol, such as a α-cyclodextrin. In certain embodiments, the co-polymer is derived form an α-cyclodextrin co-monomer which can can include 2-, 3- and 6-hydroxy groups.

The α-cyclodextrin co-polymer can be of any convenient size. In some cases, the co-polymer has an average MW of 10,000 kDa or more. In some cases, the co-polymer has an average MW of, inter alia, 10,000 kDa or less, such as 9000 kDa or less, 8000 kDa or less, 7000 kDa or less, 6000 kDa or less, 5000 kDa or less, 4000 kDa or less, 3000 kDa or less, 2000 kDa or less, 1000 kDa or less, 900 kDa or less, 800 kDa or less, 700 kDa or less, 600 kDa or less, 500 kDa or less, or even less.

The α-cyclodextrin co-polymers which find use in the functionalized supports of the present disclosure can be linear, branched or grafted. As used herein, the term "linear α-cyclodextrin co-polymer" refers to a polymer including α-cyclodextrin molecules, or derivatives thereof which are inserted within a polymer chain. As used herein, the term "grafted α-cyclodextrin co-polymer" refers to a polymer comprising α-cyclodextrin molecules, or derivatives thereof which are pendant off of the polymer chain. The term "graft polymer" as used herein refers to a polymer molecule which has additional moieties attached as pendent groups along a polymer backbone. The term "graft polymerization" denotes a polymerization in which a side chain is grafted onto a polymer chain, which side chain consists of one or several other monomers. The properties of the graft copolymer obtained such as, for example, solubility, melting point, water absorption, wettability, mechanical properties, adsorption behavior, etc., deviate more or less sharply from those of the initial polymer as a function of the type and amount of the grafted monomers. As used herein, a branched α-cyclodextrin co-polymer refers to a polymer backbone with a plurality of branch points, wherein each branch point is a starting point of yet another strand of the polymer backbone, and each section of polymer backbone can have a plurality of α-cyclodextrin molecules, or derivatives thereof, inserted into or grafted onto the chain.

The co-polymer can have a variety of different structures, such as a random network structure, a linear structure, a dendritic structure, or a brush polymeric structure. In some cases, the co-polymer has a random network structure. The co-polymer can be composed of particles, such as nano- to micron-scale particles, i.e., particles that have an average diameter in the nanometer scale or in the micrometer scale. The term "particle" as used herein refers to a solid phase such as colloidal particles, microspheres, nanoparticles, or beads. Any convenient methods for generation of such particles can be used. In some cases, the co-polymer has a porous solid structure that can be shaped or molded into any convenient form. In certain instances, the co-polymer is a porous monolithic substrate, for example, a porous solid substrate that is configured as a monolithic chromatography column or as a monolithic filter column.

In some embodiments, the co-polymer forms a thin film on a support of interest. The co-polymer can be a film that is configured on the surface of a solid support. The co-polymer can be conjugated to a solid support.

Supports

Any convenient supports can be utilized in conjunction with the subject α-CD moieties to provide a functionalized or modified (e.g., surface modified) support. As used herein, the terms "support" and "substrate" are used interchangeable and refer to an underlying substance to which the compounds and materials of the present disclosure can be attached or associated. The subject supports find use in a variety of applications. When the subject support finds use in the context of an extraction or separation method of interest, the support may be referred to herein as a "solid phase sorbent". Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support can be incorporated into a system that provides for separation of a component of interest from a sample assisted by any convenient methods, such as a manually-operated syringe, a centrifuge or an automated liquid handling system. In some cases, the support is a particle that finds use in an automated liquid handling system for the high throughput treatment of samples.

The supports can be composed of any convenient material(s) which provides stability and is capable of derivatization to attach the subject linker-alpha cyclodextrans. The material support that is underlying the subject modified supports can provide for a rigid and inert solid structure that is selected according to the particular application. In some cases, the underlying support is composed of rigid particles. In general terms, rigid particles of interest are particles that are insoluble in organic solvents and which resist phase collapse during chromatography. In some cases, the support is composed of cellulose acetate. In some cases, the support is composed of inorganic oxide particles. Inorganic oxide particles of interest, but are not limited to, silica, alumina, titania and zirconia particles. In certain embodiments, the support is a polymer. Any convenient polymeric support can be utilized. Polymeric supports of interest can include a cross-linked polymer or co-polymer composed of polystyrene, polyacrylate, polymethacylate, polypyrole, polypropylene or polyethylene that are typically used in chromatographic or sample preparation that is modified with a convenient functional group.

It is understood that a variety of methods (e.g., as described herein) can be used in characterizing the subject particles. Particle characterization measurements can be collected on a single particle or on a plurality of particles in a composition. Multiple particle characterization measurements can be collected on a single particle or on a plurality of particles to arrive at a distribution from which any convenient statistical metrics can be calculated. Any convenient methods for measuring and characterizing a particle or a composition of a plurality of particles can be utilized in conjunction with the subject particles and methods.

The methods and linkers described herein can be utilized to prepare a support that is surface modified with a thin film of the α-cyclodextrin moiety. In certain instances, the thin film comprises a monolayer of the α-cyclodextrin moiety attached to the surface of a support. In certain instances, the support is a particle. In certain cases, the support is composed of silica particles.

Attachment Chemistries and Linkers for Modifying Supports

Any convenient methods and materials can be utilized in preparing a modified support including a linked α-cyclodextrin moiety. A variety of supports of various formats (e.g., planar surface, beads, particles, pins) are available with a variety of surface chemistries to which any of the subject linkers and/or α-cyclodextrin moieties can be attached. In some instances, the support for modification is a support having amine or hydroxyl functional groups at the surface suitable for derivatization, e.g., via any convenient chemistry.

Figure 2:
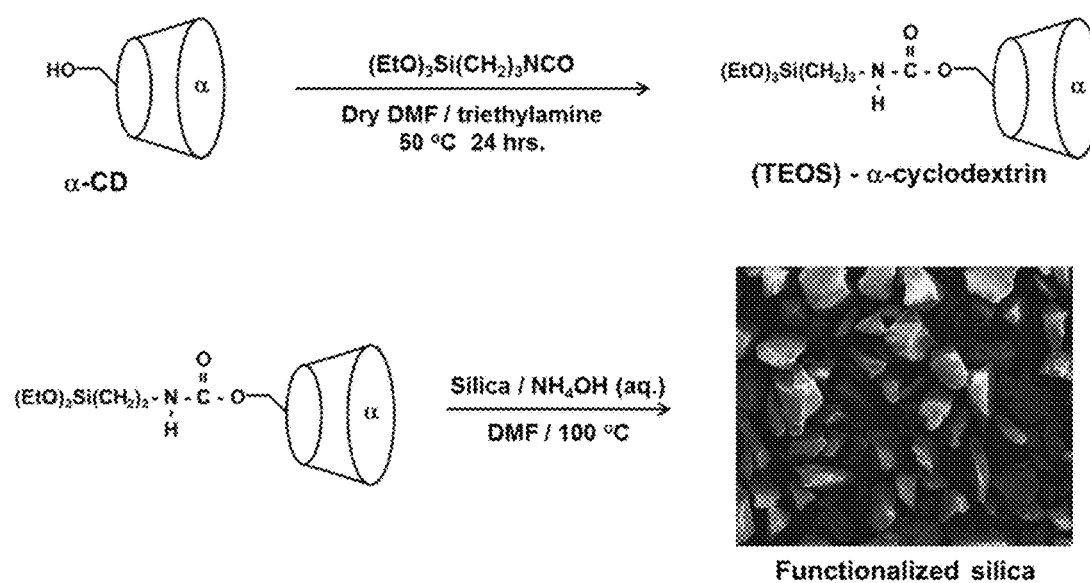
FIG. 2 illustrates an exemplary synthetic strategy for the covalent attachment of α-cyclodextrin to nanoporous silica using 3-(triethoxysilyl)propyl isocyanate as a linker group (e.g., Method I).
Figure 3:
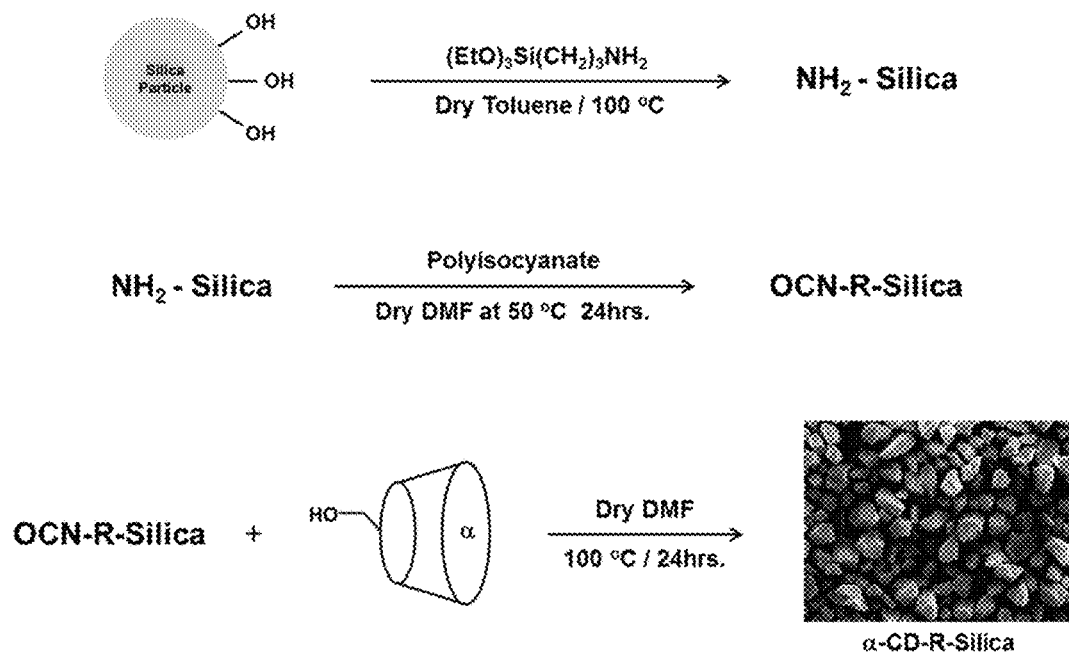
FIG. 3 shows a synthetic strategy for the covalent attachment of α-cyclodextrin to nanoporous silica using a variety of isocyanate molecules as linker groups (e.g., Method II).

In some instances, a functionalized silane linker chemistry is used (see e.g., Method I is the examples described herein) to attach an α-cyclodextrin moiety of interest to a silica support, e.g., a silica particle(s). Exemplary amino silane linkers of interest include, but are not limited to, $(EtO)_3Si(CH_2)_3NCO$, $(EtO)_3Si(CH_2)_3NH_2$ and derivatives thereof. FIG. 2 illustrates one configuration of a method of preparing a functionalized silica support using a silane linker $((EtO)_3Si(CH_2)_3NCO)$ to attach an α-cyclodextrin moiety to the surface. FIG. 3 illustrates an alternate method of preparing a functionalized silica support using a silane linker $((EtO)_3Si(CH_2)_3NH_2)$ to attach an α-cyclodextrin moiety to the surface.

Figure 4:
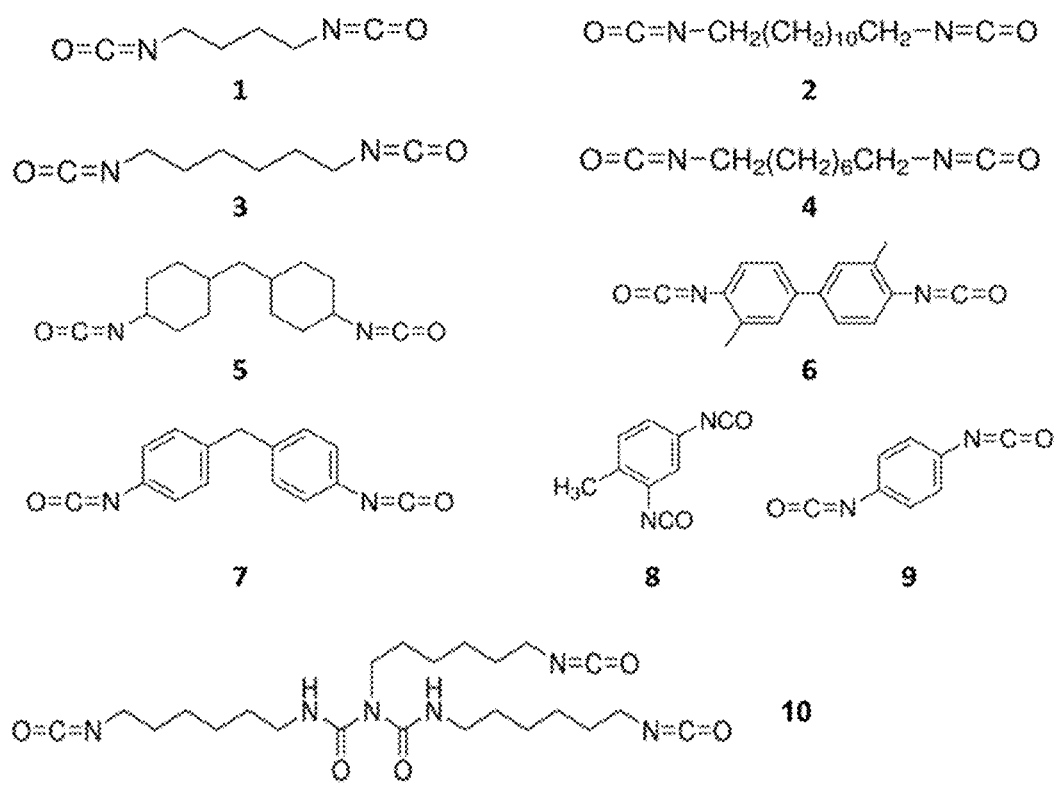
FIG. 4 illustrates exemplary isocyanate linker molecules useful for the bonding of α-CD onto amino-functionalized silica surfaces ($NH_2$-Silica). Multiple isocyanate functionality on each molecule provide for reaction with surface amino groups present on the silica and a secondary reaction with anhydrous α-CD to covalently attach the cyclodextrin to the surface.
Figure 5:
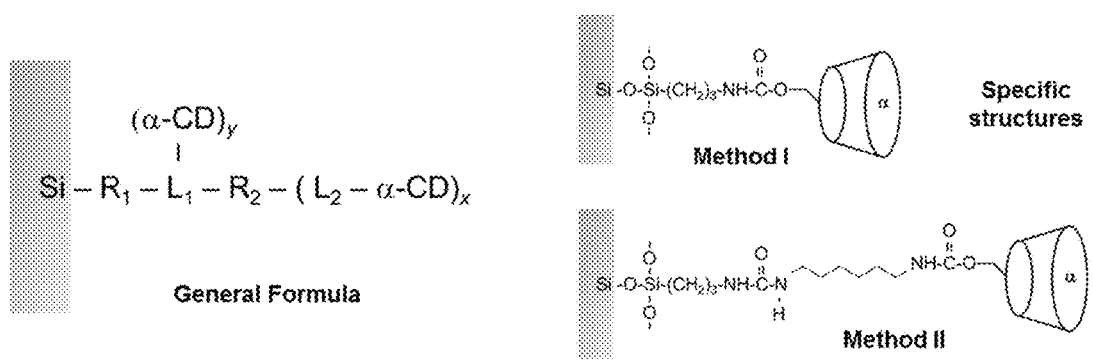
FIG. 5 illustrates a general formula and exemplary structures of interest for α-cyclodextrin bonded phases deposited onto the surface of silica through the use of Methods I and II where: x and y can be 0 or any integer; $R_1$ is any variation of 3-(triethoxysilyl)propyl isocyanate (Method I) or aminosilane incorporating primary and secondary amine groups (Method II); $L_1$=is selected from —N(R')C(=O)—, —N(R')C(=O)O—, —N(R')C(=S)—, —N(R')C(=S)O—, —N(R')C(=O)N(R')—, —N(R')C(=S)N(R')—, —CO—, —$CO_2$—, —NR'—, and —O— wherein each R' is independently H, a lower alkyl or a substituted lower alkyl; $R_2$=Any possible alkyl, aryl or other organic spacer group arising from reaction with diisocyanate, triisocyanate, oligomeric, or polyisocyanate monomers of the general formula R—(NCO)$_x$; and $L_2$=is selected from —N(R')C(=O)—, —N(R')C(=O)O—, —N(R')C(=S)—, —N(R')C(=S)O—, —N(R')C(=O)N(R')—, —N(R')C(=S)N(R')—, —CO—, —$CO_2$—, —NR'—, and —O— wherein each R' is independently H, a lower alkyl or a substituted lower alkyl.

In certain embodiments, a divalent linker chemistry is used to connect an amino functionalized surface of a support to a hydroxyl or amino group of an α-cyclodextrin moiety of interest. A variety of linking chemistries are available to conjugate a linker to an amino support. In some instances, the method is performed in a stepwise fashion, e.g., where the amino support is conjugated to the linker, which is subsequently derivatized with the α-cyclodextrin moiety in a separate step. In certain instances, the α-cyclodextrin moiety is conjugated with the linker which is subsequently conjugated to the amino support. In certain cases, isocyanate or isothiocyanante chemistry is used at each step. In some cases, a divalent or multivalent polyisocyanate linker reagent is utilized in the preparation of the subject support. FIG. 4 shows some exemplary polyisocyanate linker reagents (e.g., linkers 1-10) that can be utilized in the preparation of the subject modified supports.

The α-cyclodextrin moiety can be linked to the surface of a support via a carbamate, a thiocarbamate, an ester, an amide, a thioamide, a urea, a thiourea, an amino, a keto, or an ether linking group. In certain embodiments, the support is silica particles. In some instances, the subject support includes particles that comprise the structure:

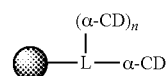

wherein: L is a linker; α-CD is a α-cyclodextrin moiety; and n is 0, or an integer from 1 to 6. In certain cases, n is 0 such that the linker is divalent and attached to one α-cyclodextrin moiety. In some cases, n is 1, such that the linker is branched and trivalent.

In certain embodiments, the subject support includes particles that comprise the structure:

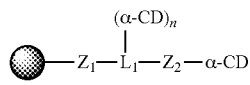

wherein: $L_1$ is a linker; $Z^1$ and $Z^2$ are linking functional groups independently selected from carbamate, thiocarbamate, ester, amide, thioamide, urea, thiourea, amino, keto and ether; α-CD is a α-cyclodextrin moiety and n is 0, or an integer from 1 to 6. In certain cases, n is 0 such that the linker is divalent and attached to one α-cyclodextrin moiety. In some cases, n is 1, such that the linker is branched and trivalent. In some instances, $Z^1$ and $Z^2$ are different. In some instances, $Z^1$ and $Z^2$ are the same. In some instances, $Z^1$ and $Z^2$ are selected from carbamate and thiocarbamate, urea and thiourea. In some instances, $Z^1$ and $Z^2$ are selected from carbamate, thiocarbamate, amide, thioamide, urea, thiourea, and ether. In certain cases, the particles are silica particles.

In certain embodiments, the subject support includes particles that comprise the structure:

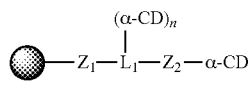

wherein:
the particles are silica particles (e.g., silica particles derivatized with an amino silane group, such as —Si—O—Si-alkyl-NR'—);
$Z^1$ and $Z^2$ are independently selected from —N(R')C(=O)—, —N(R')C(=O)O—, —N(R')C(=S)—, —N(R')C(=S)O—, —N(R')C(=O)N(R')—, —N(R')C(=S)N(R')—, —CO—, —CO$_2$—, —NR'—, —C(=S)—, —C(=S)O—, —C(=O)N(R')—, —C(=S)N(R')—, and —O— wherein each R' is independently H, a lower alkyl or a substituted lower alkyl;
$L_1$ is a $C_1$-$C_{20}$ alkyl, $C_1$-$C_{20}$ substituted alkyl, $C_1$-$C_{20}$ aryl, $C_1$-$C_{20}$ substituted aryl, $C_1$-$C_{20}$ heteroaryl, $C_1$-$C_{20}$ substituted heteroaryl or a PEG linking group; and α-CD is the α-cyclodextran moiety.

In certain cases, n is 0. In some cases, n is 1. In certain instances, each R' is H or lower alkyl. In certain instances, each R' is H. In certain instances, $L_1$ is a $C_1$-$C_{20}$ alkyl, $C_1$-$C_{20}$ aryl, or a PEG linking group.

It is understood that atoms or groups associated with the starting support (e.g., amino or hydroxyl surface groups) can become part of linking functional groups that connect to the α-cyclodextran moieties. As such, it is understood that in some cases, such atoms and groups are meant to be included in the formula and names of linking functional groups (e.g., $Z_1$ and $Z_2$) described herein.

In certain embodiments, the subject support includes particles that comprise the structure:

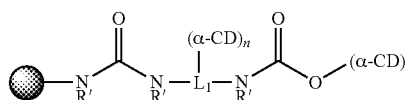

wherein each R' is independently H, alkyl or substituted alkyl. In certain cases, n is 0. In some cases, n is 1. In certain instances, each R' is H or lower alkyl. In certain instances, each R' is H. In certain instances, $L_1$ is a $C_1$-$C_{20}$ alkyl, $C_1$-$C_{20}$ aryl, or a PEG linking group.

In certain embodiments of the structures above, α-CD is linked to the particle via a hydroxyl. In certain cases, the hydroxyl is selected from a 6-hydroxyl, a 3-hydroxyl and a 2-hydroxyl group. In certain cases, the particles include α-CD groups that are linked via a variety of functional groups, e.g., one or more hydroxyl groups selected from a 6-hyhroxyl, a 3-hydroxyl and a 2-hydroxyl group.

In certain embodiments of the structures above, $L_1$ is selected from:

a) —(CH$_2$)$_m$— where m is an integer from 2 to 12 (e.g., 4, 6, 8, or 12);

b)

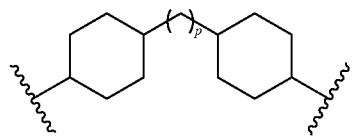

wherein p is 0 or an integer from 1 to 6 (e.g., 1);

c)

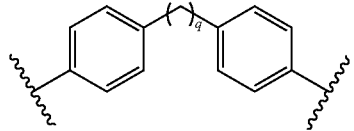

wherein q is 0 or an integer from 1 to 6 (e.g., 1);

d)

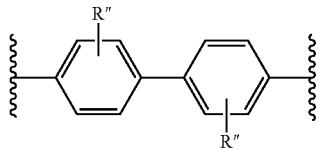

wherein each R" is an optional substituent (e.g., each R" is a methyl substituent ortho to the adjacent linked group);

e)

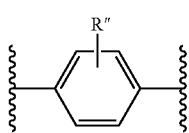

wherein R" is an optional substituent (e.g., R" is absent); and
f)

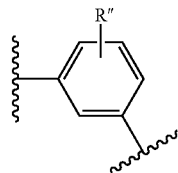

wherein R" is an optional substituent (e.g., R" is a methyl substituent); and
g)

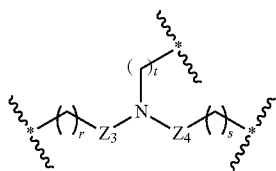

wherein r, s and t are independently an integer from 2 to 12 (e.g., r, s and t are independently 4, 6, 8, or 12). In certain embodiments, $L_1$ is linker a). In certain embodiments, $L_1$ is linker b). In certain embodiments, $L_1$ is linker c). In certain embodiments, $L_1$ is linker d). In certain embodiments, $L_1$ is linker e). In certain embodiments, $L_1$ is linker f). In certain embodiments, $L_1$ is linker g).

In certain embodiments of the subject support, the linked α-cyclodextran moiety is described by the structure (XI) or (XII):

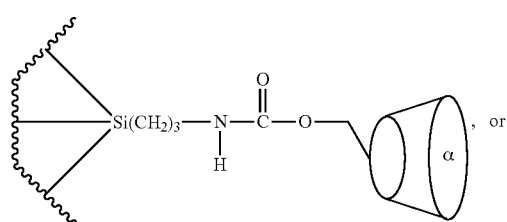

(XI)

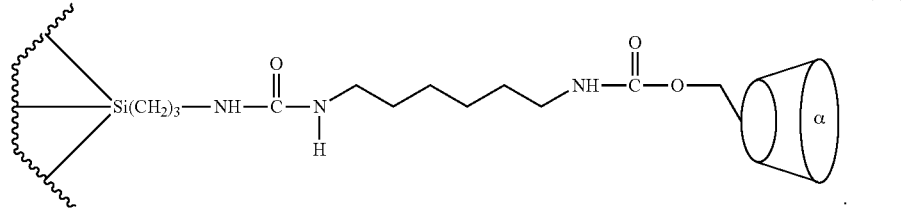

(XII)

It is understood that any of the $L_1$ linker groups a) to f) can be inserted into the formula (XII) to replace the C6 alkyl group depicted.

Blends

In some cases, the subject modified supports are composed of particles that can be blended with any other convenient particulate supports, e.g., particles having a particular functionality or property of interest, to provide a blended composition. In some cases, the modified supports and blended compositions thereof find use in a separation or extraction application of interest, and can be referred to as a solid phase sorbent.

Blending the subject modified particles with sorbents containing different functionality can also provide desirable properties. The blending ratios and materials can be varied as need to provide a desirable property of interest. Sorbents that can be blended with αCD functionalized particles (e.g., silica) include, but are not limited to, C18, primary secondary amine (PSA), graphitized carbon black (GCB), weak and strong cation exchangers (e.g. phenol, carboxylic acid, sulfonic acid), and weak and strong anion (e.g. amine, ammonium) exchangers. C18 on silica produces a blend of interest with αCD functionalized silica for the removal of matrix co-extractives (e.g. lipids) from various sample extracts in an SPE cartridge. The αCD on silica/C18 ratio can be selected based on the αCD and carbon loading. The blending of a C18 sorbent with the subject modified silica particles provides for the use of lower water content (e.g., 20% versus 50%) in the subject methods of sample preparation. In some cases, this provides for desirable conditions for e.g., protein precipitation (PPT) applications, increased matrix capacity, and improved phospholipid removal (e.g. 100% versus 54-94% removal) from biological samples. In some cases, a lower water content also improves the solubility of hydrophobic analytes and allows the final eluent to be easily evaporated or dried when necessary (e.g. GC applications).

In some cases, the subject solid phase sorbent comprises a blend of particles that are surface modified with an α-cyclodextrin moiety with C18 modified silica particles in a ratio of 1:10 to 10:1 by weight, such as a ratio of about 2:1.

Systems

Aspects of the present disclosure include systems for analytical sample treatment or preparation. The system can include a container having disposed therein a solid phase sorbent including an α-cyclodextrin-modified support (e.g., a particulate composition, as described herein). In some embodiments of the system, the composition includes rigid particles that are surface modified with an α-cyclodextrin moiety. Any of the subject supports including an α-cyclodextrin moiety can be utilized in the systems of the present disclosure as a solid phase sorbent.

As used herein, the term "container" refers to a discrete container that can be isolated or can be one of an arrangement of containers (e.g., wells, vials, tubes, columns, cartridges, syringes, pipette tips, etc. in a multi-well tray). In certain embodiments, the system includes two or more containers, such as 6 or more, 12 or more, 24 or more, 48 or more, 96 or more or 384 or more discrete containers. Each container of the system can include the same or different analytical sample treatment composition. Depending on the number of containers in the subject system, the number of analytical sample treatment compositions can vary, as desired, such as two or more, three or more, or four or more and including five or more analytical sample treatment compositions. In some instances, the system includes a plurality of the containers, where at least one of the containers includes a solid phase sorbent. The plurality of the containers can be configured as a multi-well plate. In some instances, one or more of the plurality of the containers can lack solid phase sorbent, e.g., the container can be empty or include a control composition, and as such can find use as a negative control in any convenient application of interest.

Figure 10:
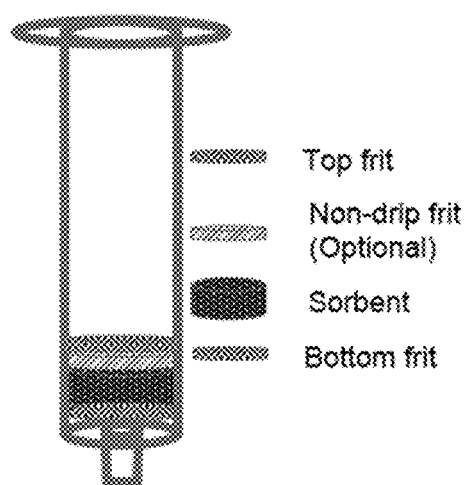
FIG. 10 shows an exemplary cartridge system having a frit stack configuration for use with a SPE workflow method.

In certain embodiments, the container is one that is configured to have a fluid inlet and outlet is suitable for use in a flow though application, e.g., a cartridge, column, tube, pipette tip, syringe, etc. FIG. 10 illustrates a schematic of one configuration of a system of interest. The container may further include any convenient components. Inclusion of various components depends on the particular application of interest and sample of interest in which the system may find use. In certain instances, the container comprises a non-drip frit operably connected to the solid phase sorbent that is disposed in the container between the solid phase sorbent and the fluid inlet. A non-drip frit prevents passage of a liquid through the container under normal atmospheric and gravity conditions. The non-drip frit can provide for a chamber within the container that is separated from the sorbent, and in which additional sample treatment or sample processing steps can be accomplished. For example, a protein precipitation step can be performed in such a chamber prior to filtration through a frit and application of a filtrate to the sorbent. Any convenient methods steps can be performed in such a chamber of the container. Passage of a liquid of interest though the non-drip frit can be accomplished, e.g., via centrifugation or application of positive or negative pressure to the inlet or outlets of the container.

As used herein the terms "multi-well tray" and "multi-well plate" are used interchangeably to refer to a two-dimensional array of containers, e.g., wells, vials, tubes, pipette tips, etc. that can be configured in any convenient format. Multi-well trays of interest include, but are not limited to, a construct including a configuration of wells, tubes and/or vials arranged in a series of rows and columns in a X-Y plane (e.g., 2×3, 2×6, 3×4, 8×12, 16×24), such as 12-well, 24-well, 96-well and 384-well plates or trays of containers.

The containers can be of any convenient size, such as 1 L or less, 500 mL or less, 100 mL or less, 50 mL or less, 10 mL or less, 5 mL or less, 2.0 mL or less, 1.0 mL or less, 500 µL or less, 300 µL or less, 200 µL or less, 100 µL or less or even less. Each container can have disposed therein any convenient amount of a solid phase sorbent of interest. In some cases, the solid phase sorbent disposed in the container is a dry composition, e.g., a composition that includes no solvent.

In some cases, the container includes a filter (e.g., a porous membrane) through which components of a sample which is subsequently disposed therein can be passed, e.g., by application of positive or negative pressure, by centrifugation, by gravity filtration. In some cases, the container is a filter tube. Any convenient filters and membrane types can be incorporated into the subject containers. Filters of interest include, but are not limited to, size exclusion filters, lipid retaining filters, chromatography supports, affinity filters, affinity supports, and the like. In some cases, container includes a lipid retaining membrane. Any convenient materials can find use in the subject containers to provide for filtering of the components of a sample disposed therein, such as CPG, C8, C18, carbon, affinity chromatography supports, and the like. Any filtering means can be utilized, such as filters from Millipore, Porex, Advantec, and the like, so long as the pore size utilized is appropriate for the application. Similarly, filters of polypropylene, PVDF, PTFE, nitrocellulose, regenerated cellulose, etc., can be utilized, as desired for particular applications.

Kits and Devices

Aspects of the present disclosure include separation devices including the subject α-cyclodextrin-modified supports. In some cases, the support is a particulate composition that can be utilized with any convenient separation devices having a stationary phase. Devices of interest include, but are not limited to, a chromatography column, a chip, a solid phase extraction media, a pipette tip and a disk.

Also provided by the present disclosure are kits for practicing the subject methods, as described herein. The subject kits at least include an α-cyclodextrin modified support. As discussed herein, the subject supports can be provided as a system disposed in a single container or disposed in an array of containers. Other optional components of the kit include, but are not limited to QuEChERS extraction salts, an analyte extraction solvent, a quantitation standard, a porous membrane filer and a precipitation solvent.

The various components of the kit can be present in separate containers or certain compatible components can be pre-combined into a single container, as desired. The subject kits can also include one or more other reagents for preparing or processing an analyte sample. The reagents can include one or more matrices, solvents, sample preparation reagents, buffers, desalting reagents, enzymatic agents, denaturing reagents, where calibration standards such as positive and negative controls can be provided as well. As such, the kits can include one or more containers such as vials or bottles, with each container containing a separate component for carrying out a sample processing or preparing step and/or for carrying out one or more steps of a sample preparation and analysis protocol. In addition, the kits can also include one or more control analyte mixtures, e.g., two or more control samples for use in testing the kit.

In addition to above-mentioned components, the subject kits can further include instructions for using the components of the kit to practice the subject methods, i.e., to prepare a sample and/or assess a sample. The instructions for practicing the subject methods are generally recorded on a suitable recording medium. For example, the instructions can be printed on a substrate, such as paper or plastic, etc. As such, the instructions can be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods Aspects of the present disclosure include methods of extracting a component of interest from a sample. Any convenient components of a sample can targeted for separation or extraction from the sample. In some cases, the component is a target analyte, and the subject method includes separating the component from the sample so that it can be isolated. The target component can then be detected, quantitated and/or further analyzed using any convenient methods. In certain instances, the component of interest which is extracted from the sample is an agent which can interfere with the analysis of the target analyte, e.g., by decreasing the sensitivity of the analytical method or by masking or reducing the effective amount of analyte in the sample.

In some embodiments, the method includes contacting a sample with an α-cyclodextrin modified support (e.g., as described herein) to bind matrix-interfering agents of interest, if present in the sample, to the support. The contacted sample can be incubated for any convenient time under suitable conditions depending on the sample. In the contacted sample, the α-cyclodextrin moiety that is attached to the support is capable of forming a complex with a target component of the sample, thereby binding the component to the support and selectively removing the component from the remaining contacted sample.

Any convenient methods of sample preparation, cleanup and analysis can be adapted to include the subject methods and compositions. Methods of interest include, but are not limited to, those methods for reducing matrix effects described in U.S. Pat. No. 7,999,084, the disclosure of which is herein incorporated by reference, QuECHERS protocols, and protein precipitation methods. Any convenient methods and formats that find use in treating or processing analytical samples can be adapted for use with the subject methods. In some embodiments, the methods are performed in a Dispersive Solid Phase Extraction (dSPE) format. In a dSPE format, the subject support is suspended in the sample, which is optionally diluted in a convenient diluent. In some embodiments, the methods are performed in a conventional Solid Phase Extraction (SPE) format. In a SPE format, the optionally diluted sample is added to the immobilized support (e.g., a bed of particles in a column format) and eluted from the support in a flow through mode, e.g., via column chromatography.

In certain cases, the target component is a component that is desirable to remove from the sample (e.g., a matrix interfering agent). Removal of the target component from the sample produces a contacted sample that can include a target analyte that is to be analyzed. As such, in some cases the method is a method of reducing matrix effects in an analytical sample. In some cases, the presence of the target component in the sample can have a deleterious effect on the analysis of the target analyte and removal of the undesirable co-extractives provides for an improved analysis of the target analyte. The analytical sample (e.g., as described herein) can be one that includes a matrix-interfering agent and an analyte.

As used herein, the term "matrix" refers to the components of a sample other than the analyte of interest. The matrix can have a considerable effect on the way the analysis is conducted and the quality of the results obtained—such effects are called matrix effects in mass spectrometry.

As used herein, the term "matrix interfering agent" refers to any substance present in an analytical sample that causes matrix effects, that is, interferes with quantitation of an analyte, or results in accumulation, contamination and/or degradation to the analytical system. Matrix interfering agents commonly suppress the ionization of a particular analyte present in the sample during electrospray ionization for mass spectrometric analysis. The relative abundance of the analyte can be underrepresented and/or underestimated or overrepresented relative to its true abundance in the sample due to matrix effects. Any convenient matrix-interfering agent that is present in the sample can be selected for removal via the subject methods. Matrix interfering agents of interest include, but are not limited to, lipids (such as cholesterol, triglycerides, phospholipids, lypophsosplipids, lipoproteins), surfactants, excipients, polyethylene glycol (PEG), disintegrants and dosing agents. In some embodiments, the lipids are phospholipids. In certain instances, the surfactants are selected from anionic surfactants or nonionic surfactants. In some cases, the surfactants include a hydrocarbon chain which can be advantageously complexed using the α-cyclodextrin modified supports described herein. The method can include contacting the analytical sample with an α-cyclodextrin modified support (e.g., as described herein) to produce a contacted sample including matrix interfering agents bound to the support. In some cases, the matrix-interfering agent is a lipid and the complex comprises a lipid-α-cyclodextrin complex.

Surfactants that can be removed using the presently described supports and methods include a wide variety of surfactants, including nonionic surfactants as well as ionic surfactants, including cationic surfactants, anionic surfactants or zwitterionic surfactants. Nonionic surfactants include, for example, polyoxyl stearates such as polyoxyl 40 stearate, polyoxyl 50 stearate, polyoxyl 100 stearate, polyoxyl 12 distearate, polyoxyl 32 distearate, and polyoxyl 150 distearate, and other series of surfactants, triblock co-polymers of ethylene oxide/propylene oxide/ethylene oxide, also known as poloxamers, having the general formula $HO(C_2H_4O)_a(—C_3H_6O)_b(C_2H_4O)_aH$, sugar ester surfactants, sorbitan fatty acid esters such as sorbitan monolaurate, sorbitan monopalmitate, sorbitan monostearate, sorbitan tristearate, and other Span™ series surfactants, glycerol fatty acid esters such as glycerol monostearate, polyoxyethylene derivatives such as polyoxyethylene ethers of high molecular weight aliphatic alcohols (e.g., 30, 35, 58, 78 and 99) polyoxyethylene stearate (self-emulsifying), polyoxyethylene 40 sorbitol lanolin derivative, polyoxyethylene 75 sorbitol lanolin derivative, polyoxyethylene 6 sorbitol beeswax derivative, polyoxyethylene 20 sorbitol beeswax derivative, polyoxyethylene 20 sorbitol lanolin derivative, polyoxyethylene 50 sorbitol lanolin derivative, polyoxyethylene 23 lauryl ether, polyoxyethylene 2 cetyl ether with butylated hydroxyanisole, polyoxyethylene 10 cetyl ether, polyoxyethylene 20 cetyl ether, polyoxyethylene 2 stearyl ether, polyoxyethylene 10 stearyl ether, polyoxyethylene 20 stearyl ether, polyoxyethylene 21 stearyl ether, polyoxyethylene 20 oleyl ether, polyoxyethylene 40 stearate, polyoxyethylene 50 stearate, polyoxyethylene 100 stearate, polyoxyethylene derivatives of fatty acid esters of sorbitan such as polyoxyethylene 4 sorbitan monostearate, polyoxyethylene 20 sorbitan tristearate, and other series of surfactants, phospholipids and phospholipid fatty acid derivatives such as fatty amine oxides, fatty acid alkanolamides, propylene glycol monoesters and monoglycerides, such as hydrogenated palm oil monoglyceride, hydrogenated soybean oil monoglyceride, hydrogenated palm stearine monoglyceride, hydrogenated vegetable monoglyceride, hydrogenated cottonseed oil monoglyceride, refined palm oil monoglyceride, partially hydrogenated soybean oil monoglyceride, cotton seed oil monoglyceride sunflower oil monoglyceride, sunflower oil monoglyceride, canola oil monoglyceride, succinylated monoglycerides, acetylated monoglyceride, acetylated hydrogenated vegetable oil monoglyceride, acetylated hydrogenated coconut oil monoglyceride, acetylated hydrogenated soybean oil monoglyceride, glycerol monostearate, monoglycerides with hydrogenated soybean oil, monoglycerides with hydrogenated palm oil, succinylated monoglycerides and monoglycerides, monoglycerides and rapeseed oil, monoglycerides and cottonseed oils, monoglycerides with propylene glycol monoester sodium stearoyl lactylate silicon dioxide, diglycerides, triglycerides, polyoxyethylene steroidal esters, TRITON-X series of surfactants produced from octylphenol polymerized with ethylene oxide, where the number "100" in the trade name is indirectly related to the number of ethylene oxide units in the structure, (e.g., X-100™ has an average of N=9.5 ethylene oxide units per molecule, with an average molecular weight of 625) and having lower and higher mole adducts present in lesser amounts in commercial products, as well as compounds having a similar structure to X-100™, including CA-630™ (octylphenoxypolyethoxyethanol) and P-40M (NP-40™, N-lauroylsarcosine, Sigma Chemical Co., St. Louis, Mo.), and the like. Any hydrocarbon chains in the surfactant molecules can be saturated or unsaturated, hydrogenated or unhydrogenated. Sugar ester surfactants include sugar fatty acid monoesters, sugar fatty acid diesters, triesters, tetraesters, or mixtures thereof.

In some cases, the target component of the sample that is extracted using the subject supports can be a target analyte that is to be analyzed. Complexation of the target analyte by the α-cyclodextrin modified support allows for separation of the target analyte from the matrix of the sample (e.g., as described herein) and can provide for an improved analysis of the target analyte. In such cases, the target analyte can be subsequently dissociated from the support, prior to detection.

Any convenient sample can be treated according to the subject methods. The term "sample" as used herein relates to a material or mixture of materials, in some cases, although not necessarily, in fluid, i.e., aqueous, form, containing one or more components of interest. Samples can be derived from a variety of sources such as from food stuffs, environmental materials, a biological sample or solid, such as tissue or fluid isolated from an individual. The term "biological sample" is used herein to refer to a whole organism, plant, fungi or a subset of animal tissues, cells or component parts which can in certain instances be found in blood, mucus, lymphatic fluid, synovial fluid, cerebrospinal fluid, saliva, amniotic fluid, amniotic cord blood, urine, vaginal fluid and semen, and also samples of in vitro cell culture constituents (including but not limited to conditioned medium resulting from the growth of cells in cell culture medium, putatively virally infected cells, recombinant cells, and cell components).

In some cases, one or more preparatory steps are performed on the sample before the sample is treated according to the subject methods, such as any convenient combination of liquid phase extraction, solid phase extraction, filtration, centrifugation, dilution or concentration steps. In certain instances, the sample is a liquid extract of a sample of interest, such as a food sample, an environmental sample or a biological sample. In some cases, the sample is a QuEChERS extract.

In general terms, the QuEChERS extraction protocol can consist of three simple steps. A sample (ground solid or liquid) is added to a centrifuge tube. The extraction step (Step 1) involves the addition of acetonitrile and in some cases water to the sample that is spiked with QC and internal standards. Then, salts are added to induce partitioning of the acetonitrile and aqueous phases. The mixture is mixed/shaken. The clean-up step (Step 2) involves the transfer of the acetonitrile layer containing sample coextractives and analytes of interest to a tube containing the Dispersive Solid Phase Extraction (dSPE) materials or to a column of such materials. These materials can remove unwanted coextractives via dSPE or SPE methods. In some cases, such materials include C18, graphitized carbon black (GCB), zirconia, primary/secondary amine (PSA) or in the case of this present disclosure, α-CD modified supports. The resulting slurry is mixed and centrifuged. The final step (Step 3) is the LC chromatographic separation and quantitation of the sample components in the supernatant.

Additional sample clean up can be required for some applications such as GC. If so, the supernatant from the dSPE or SPE can be transferred to a tube containing additional inorganic salts. The slurry is mixed and centrifuged. The supernatant resulting from the second cleaning step is then separated and quantitated by the chromatographic method.

Protein precipitation consists of addition of acetonitrile and/or methanol to the sample to precipitate the unwanted proteins. The precipitate can be removed by filtration or centrifugation. Filtration is accomplished by passing through small porosity filters and in some cases, sorbent materials to remove unwanted coextractives.

Components in a sample that are of interest for downstream detection and/or analysis can be termed "analytes". In some embodiments, the sample is a complex sample containing at least about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $10^9$, $10^{10}$, $10^{11}$, $10^{12}$ or more species of analyte. The term "analyte" refers to a known or unknown component of a sample. In some cases, analytes are biopolymers, i.e., an oligomer or polymer such as an oligonucleotide, a peptide, a polypeptide, an antibody, or the like. In some cases, an analyte is a small (e.g., 1000 Da or less, such as 500 Da or less) organic compound, such as an environmental pollutant, e.g., a pesticide or a drug.

Once the target component has been bound to the α-cyclodextrin modified support, the support can be separated from the sample using any convenient methods, including but not limited to, filtration, centrifugation, and washing via column chromatography. Any desirable solvents can be selected to be utilized in, or added to, the sample or support to provide for the separation of the support-bound component of interest. In certain instances, the α-cyclodextrin modified support is separated from the contacted sample via filtration, with optionally washing steps.

The contacting step can be performed by adding an amount of α-cyclodextrin modified support effective to complex and bind all of the target component (e.g., a target analyte or matrix interfering agents) in a sample. The α-cyclodextrin modified support can be added to the sample (or vice versa) as a solution in any convenient solvent. The contacting can be performed for any convenient period of time, e.g., from about 10 seconds to about 60 minutes, such as from about 10 seconds to about 10 minutes, e.g., for about 1 minute, about 2 minutes, about 5 minutes, or about 10 minutes.

Contacting the sample with the α-cyclodextrin composition can include mixing. Any convenient method can be employed to stir the sample with the α-cyclodextrin composition. Mixing can include, for example stirring with a magnetic stir bar or manually stirred using any convenient stirring apparatus. Alternatively, the sample can be stirred by vortexing the contacted sample, shaking the contacted sample such as with a mechanical shaker or shaking can be manually performed (i.e., by hand). In some instances, mixing the sample with the α-cyclodextrin composition includes sonicating the contacted sample.

In some cases, the contacting includes eluting the sample through a porous membrane/frit. The separating step can include filtering the sample through a porous membrane/frit. The support can be separated from the contacted sample because it is immobilized in a container (e.g., cartridge or chromatography column) or as part of a porous membrane.

In certain cases, the sample is a biological sample and the contacting step can also lead to precipitation of non-complexing components. The sample can include protein components which do not complex the α-cyclodextrin modified support. In some cases, the separating step further includes filtering precipitated proteins from the contacted sample. In some embodiments, a sample is subjected to a protein precipitation treatment followed by centrifugation, or does not contain sufficient protein to warrant removal prior to analysis, and subsequently is contacted with the α-cyclodextrin modified support with selectivity for matrix interfering agents. In some cases, the supernatant is transferred from the protein pellet using a pipette tip or a filter tube loaded with the α-cyclodextrin modified support.

The methods can further include optionally washing the cyclodextrin modified support with a wash solvent or mixture of solvents to remove unbound components. In some cases, the methods can further include eluting components from the cyclodextrin modified support with eluting solvents to release the bound components from the complex.

In some instances, separation of the support from the contacted sample produces a matrix-reduced composition that includes a reduced amount of matrix interfering components relative to the original analytical sample.

In some embodiments, the α-cyclodextrin modified support binds at least 50% of the target matrix interfering agent(s) present in the analytical sample (such as, inter alia, at least 60%, at least 70%, at least 80%, at least 90%, at least 95%, at least 98%, at least 99%, at least 99.5%, at least 99.9%). In some embodiments, the subject methods provide recovery of at least 80% of the analyte(s) in the contacted sample, such as, inter alia, at least 85%, at least 90%, at least 91%, at least 92%, at least 93%, at least 94%, at least 95%, at least 96%, at least 97%, at least 98%, at least 99%, at least 99.5%, at least 99.9%, relative to a control sample. In some embodiments of the subject methods, the α-cyclodextrin modified support includes at least 5% α-cyclodextrin relative to α-cyclodextrin moiety by weight (e.g., inter alia, at least 6%, at least 7%, at least 8%, at least 9%, at least 10%, at least 13%, at least 14%, at least 15%, at least 16%, at least 17%, at least 18%, at least 19%, at least 20%, at least 25%, at least 30 α-cyclodextrin by weight relative to the underlying support).

In some cases, the method produces a contacted sample that is substantially free from target matrix interfering agent(s). By substantially free from target matrix interfering agent(s) is meant a solution that includes 0.5% or less by weight of the agent(s), such as, inter alia, 0.1% or less by weight, 0.03% or less by weight, 0.01% or less by weight, 0.003% or less by weight, 0.001% or less by weight, 0.0003% or less by weight, or 0.0001% or less by weight.

In some cases, the method produces a contacted sample that has a reduced amount of target matrix interfering agent(s). By reduced amount of target matrix interfering agent(s) is meant a solution that includes 50% or less by weight of the agent(s), such as, inter alia, 40% or less by weight, 30% or less by weight, 20% or less by weight, 10% or less by weight, 9% or less by weight, 8% or less by weight, 7% or less by weight, 6% or less by weight, 5% or less by weight, 4% or less by weight, 3% or less by weight, 2% or less by weight, or 1% or less by weight.

Aspects of the methods include detecting a target analyte. In some cases, where the matrix interfering agents are separated from the contacted sample, the detecting includes detecting the analyte in the matrix-reduced composition that is produced. In such cases, the matrix-reduced composition has a reduced deleterious effect on the detecting the analyte. A deleterious effect refers to an undesirable reduction in the accuracy of detection, that can occur by the action of matrix interfering agents during sample preparation and/or sample analysis, e.g., by reducing the sensitivity of detector, or by undesirable removal of target analyte from the analytical sample during sample preparation. As used herein, a "reduced deleterious effect" refers to an improvement in the accuracy of analyte detection and/or quantitation, and can be determined via an improvement in one or more measures such as detection limit, signal to noise ratio, reproducibility, sensitivity, limits of quantitation, limits of detection, e.g., relative to a control sample. Any convenient methods of detecting the analyte can be used. In some cases, analyses include chromatographic, spectrophotometric, mass spectrometric, and the like, and combinations thereof. Methods of interest include, but are not limited to mass spectrometry, LC/MS-MS, and UV/vis spectroscopy.

The method can further include quantitating the amount of analyte in the sample. In some cases, the amount of analyte in the matrix-reduced composition and the amount of analyte in the sample are the same. By practicing the subject methods, the matrix interfering agent(s) can be separated from the sample without the simultaneous undesirable removal of target analyte. Separation of the matrix interfering agent(s) can provide a matrix-reduced composition that has reduced matrix effects during subsequent quantitation of the target analyte.

Mass Spectroscopic Analysis

Accordingly, the analytes and sample produced using the subject methods can be evaluated using mass spectrometry or liquid chromatography-mass spectrometry (LC-MS). The analytes can be directly analyzed. In some cases, the analyte is a protein and, the analyte can be digested into fragments prior to analysis. In some instance, the analyte is a small organic molecule, e.g., a pesticide. Accordingly, the subject analytes can be intact or fragmented (i.e., digested with an enzyme) prior to their analysis in a mass spectrometer. Prior to their analysis in a mass spectrometer, the analytical sample can also under liquid chromatography (LC). Any convenient LC methods and columns can be utilized in combination with the mass spectroscopic analysis described herein.

The samples can be analyzed using any mass spectrometer that has the capability of measuring analyte masses with high mass accuracy, precision, and resolution. Accordingly, the isolated analytes can be analyzed by any one of a number of mass spectrometry methods, including, but not limited to, electrospray mass spectrometry, matrix-assisted laser desorption ionization time-of-flight mass spectrometry (MALDI-TOF) and any tandem MS such as QTOF, TOF-TOF, etc.). Mass spectrometry methods are generally well known in the art. The basic processes associated with a mass spectrometry method are the generation of gas-phase ions derived from the sample, and the measurement of their mass.

In certain embodiments, the masses of ions produced by the analytes of interest in a sample can be calculated by methods known in the art, e.g., techniques such as selective ion monitoring (SIM) and multiple reaction monitoring (MRM) can be employed to monitor only those ions that correspond to the analytes of interest. The output from the mass spectrometry analysis can contain the masses, i.e., the molecular weights, of the isolated analytes or fragments thereof, and their relative or absolute abundances in the sample. The analyte masses obtained from mass spectrometry analysis can be compared to those expected for the analytes. By performing this comparison, any signals obtained that are not derived from the analytes of interest can be discarded, and only those signals corresponding to the pre-determined analytes can be retained. In certain embodiments, the masses of the analytes or fragments thereof are stored in a table of a database and the table usually contains at least two fields, one field containing molecular mass information, and the other field containing analyte identifiers, such as names or codes. As such, the subject methods can involve comparing data obtained from mass spectrometry to a database to identify data for an analyte of interest.

In general, methods of comparing data produced by mass spectrometry to databases of molecular mass information to facilitate data analysis is very well known in the art and, as such, need not be described here in any further detail. Accordingly, information, e.g., data, regarding the amount of analytes in a sample of interest (including information on their presence or absence) can be obtained using mass spectrometry.

For each analyte, information obtained using mass spectrometry can be qualitative (e.g., showing the presence or absence of an analyte, or whether the analyte is present at a greater or lower amount than a control analyte or other standard) or quantitative (e.g., providing a numeral or fraction that can be absolute or relative to a control analyte or other standard). Standards for assessing mass spectrometry data can be obtained from a control analyte that is present in a sample, such as an analyte of known concentration, or an analyte that has been added at a known amount to the sample, e.g., a spiked analyte. Accordingly, the data produced by the subject methods can be "normalized" to an internal control, e.g. an analyte of known concentration or the like. By comparing the results from assessing the presence of an analyte in two or more different samples using the methods set forth above, the relative levels of an analyte in two or more different samples can be obtained. In other embodiments, by assessing the presence of at least two different analytes in a single sample, the relative levels of the analytes in the sample can be obtained.

Utility

The subject compositions, kits and methods can be employed in a variety of diagnostic, analytical and research applications. The subject compositions and methods find use in any applications where the complexation and separation of a target component of a sample is desirable, e.g., to provide a sample of interest that lacks the target component, or to provide an isolated target component of interest.

Applications that involve the preparation or pre-treatment of an analytical sample for subsequent analysis are of interest. In some cases, the subject methods find use in the removal of undesirable components from analytical samples, including components that interfere with the detection and analysis of target analytes in the sample. For example, the subject compositions and methods find use in the cleanup of samples by removing matrix components such as lipids during, e.g., QuEChERS protocols of food and agricultural samples, following protein precipitation of biological samples, or extraction using dispersive solid phase extraction (dSPE).

Many complex samples (e.g. foods: avocado, oils, meats, dairy products, etc.) (e.g., biological samples) and diverse groups of analytes (e.g. pesticides, veterinary drugs, drugs of abuse, etc.) can be prepared for analysis using the subject compositions and methods. Applications of interest include, but are not limited to, multi-residue analysis, forensic/clinical analysis, and other applications that benefit from lipid removal or isolation. Removal of matrix components from such samples using the subject compositions and methods can enhance the accuracy, reproducibility, and ruggedness of analysis method as compounds that can cause potential interferences, ion suppression/enhancement, and accumulation on the chromatographic flow path and detector can be dramatically reduced or eliminated.

Other applications of interest include applications involving the elution of the trapped lipid fractions on the α-cyclodextrin stationary phase for analysis.

Figure 8:
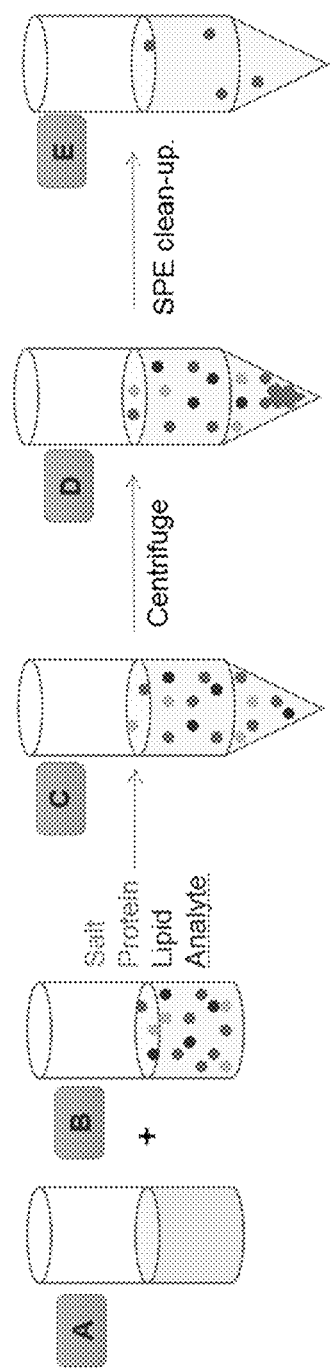
FIG. 8 illustrates a workflow scheme for protein precipitation using centrifuge in one application of the subject methods. Acetonitrile or methanol (Panel A) is added to centrifuge tube (Panel C) followed by mixing with sample (Panel B). Precipitated proteins are centrifuged to the bottom of the tube (Panel D) and the supernatant is transferred directly to an SPE tube containing clean-up sorbent and subsequently eluted to give a purified sample extract enriched in target analytes for analysis (Panel E).
Figure 9:
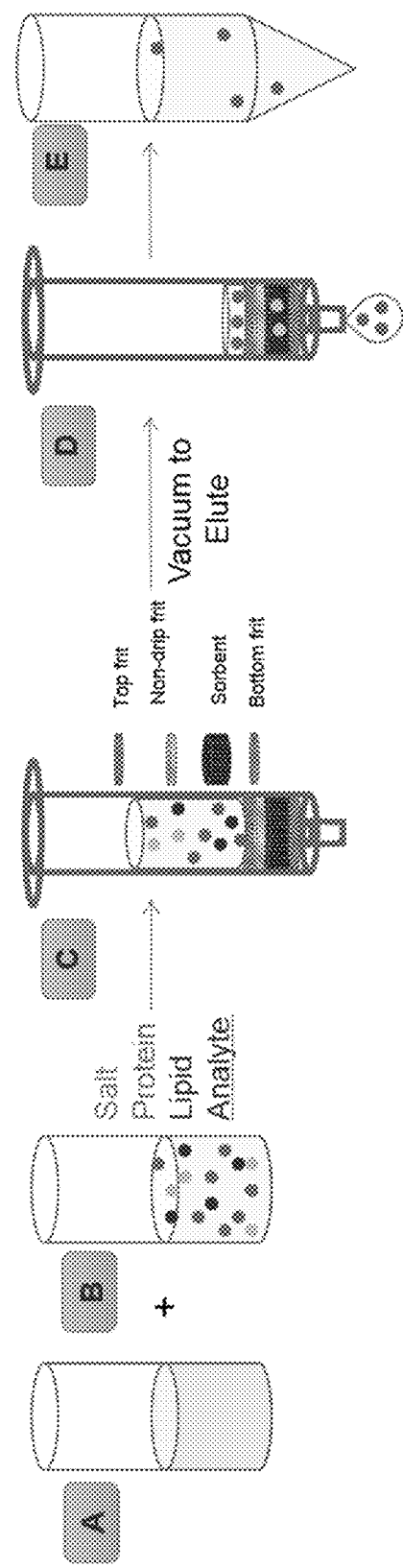
FIG. 9 illustrates a workflow scheme for protein precipitation using non-drip SPE tube. Acetonitrile or methanol (Panel A) is added to SPE tube (Panel C) containing a non-drip frit, followed by addition of sample (Panel B). Vacuum is initiated to elute the SPE tube and precipitated proteins are removed by the top frit (Panel D). Co-extracted matrix (lipids) is trapped by the sorbent (Panel D) and the eluent is collected after clean-up for analysis (Panel E).

The subject materials and methods provide practical applications in chromatographic separations, e.g., sample preparation. For example, a subject solid supported αCD provides bed stability in SPE cartridge and 96-well plate formats, where a crude extract can passed through the sorbent for removal of co-extracted matrix leaving the analytes of interest in solution for analysis as shown in FIGS. 8 and 9. Sample extract purification applications are of high interest to food, forensic, clinical, pharmaceutical, environmental, and other fields, as the removal of co-extractives reduces the possibility of matrix effects, co-eluting interferences, system contamination, carry-over, and poor reproducibility. Agilent Enhanced Matrix Removal (EMR)-Lipid implemented αCD and its co-polymer finds use for the dispersive solid phase extraction (dSPE) clean-up of sample extracts. However, use of EMR-Lipid as a stationary phase was unsuccessful due to material solubility and/or morphology changes (e.g. shrinkage, swelling, pore collapse, gelation) and resulted in poor interaction between the sample and CD units and in some cases no observable matrix removal. Methods for sample purification according to the subject methods are described herein for applications using protein precipitation (PPT) and QuEChERS workflows.

The subject materials and methods provide practical applications in biological sample preparation. For example, biological samples such as plasma can be treated according to a protein precipitation (PPT) workflow as shown in FIG. 8.

The following examples are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Synthesis and Preparation of α-CD-TEOS-Si Lipid Capture Materials

Introduction to Alpha-Cyclodextrin and Selective Capture of Lipids from Extraction Solvents Cyclodextrins (CDs) are a class of cyclic oligosaccharide which possess hydrophilic external surfaces and apolar cavities. Hydroxyl groups on the surface of a cyclodextrin (CD), in combination with the molecules hydrophobic internal cavities, promote non-covalent interactions between a variety of organic molecules and the interior surface of the cavity. These favorable interactions promote the insertion of molecules into the cavity leading to the formation of stable host-guest inclusion complexes. Due to the restricted size and shape of their cavities, cyclodextrins can selectively bind molecules which can successfully enter their interiors while excluding those molecules too large to insert and form a stable complex. Accordingly, the three most common cyclodextrin homologues (FIG. 1), α-CD (6-membered ring), β-CD (7-membered ring), and γ-CD (8-membered ring), can each be used to reversibly bind molecules of interest depending on the overall "fit" inside the cyclodextrin cavity. Cyclodextrins can form inclusion complexes with a variety of molecules and find use in enhancing drug solubility and stability, performing molecular separations, and extracting organic contaminants from water or soil samples.

TABLE 1

Basic characteristics of α, β, and γ-cyclodextrin.

|  | α-CD | β-CD | γ-CD |
| --- | --- | --- | --- |
| Number of glucose units | 6 | 7 | 8 |
| Molecular weight (g/mol) | 972 | 1135 | 1297 |
| Internal cavity diameter (Å) | 4.7-5.2 | 6.0-6.4 | 7.5-8.3 |
| Outer molecular diameter (nm) | 1.53 | 1.66 | 1.72 |
| Water solubility at 24° C. (g/L) | 145 | 18.5 | 232 |
| Water molecules bound in cavity | 6 | 11 | 17 |

Of the three most common types of cyclodextrin, it is only the α-cyclodextrin, due to its smaller 5 Å diameter cavity, which is limited to the formation of stable inclusion compounds with primarily linear molecules while excluding most other types of larger compounds. This characteristic of α-cyclodextrin provides for selective binding of the class of biomolecules known as lipids. Lipids are a group of naturally occurring compounds which includes fats, monoglycerides, diglycerides, triglycerides, and phospholipids. A common structural component of these molecules are long aliphatic chains between 4 and 24 carbons units long which can incorporate a variety of additional functional groups. The long aliphatic segment available on these biomolecules provides a hydrophobic linear component capable of insertion into α-cyclodextrin and formation of stable inclusion compounds. The larger cavities present in β—, and γ-cyclodextrin form inclusion compounds with a broader range of molecular species and consequently cannot provide selectivity for lipids alone. Thus, α-cyclodextrin's ability to complex linear alkyl chains, while simultaneously excluding larger molecules, allows for its use in the selective removal of lipids from complex matrices while excluding larger molecules of interest such as steroids, pesticides, and many other common analytes. Even when incorporated into a polymeric material, cyclodextrin retains its ability to form inclusion complexes with a wide variety of molecules.

The present disclosure provides materials which can be used in both a dSPE cleanup format and in a format which functions well as a stationary phase for flow-through (e.g., cartridge) applications. In addition, the present disclosure provides materials which can:

Incorporate high loading of α-cyclodextrin for rapid and effective lipid removal;
Incorporate high surface area and porosity to increase the absorption activity of the material;
Display hydrophilic surface properties for efficient wetting and penetration by matrix;
Remain insoluble in all common solvents and demonstrate high stability with no morphological changes; and/or
Utilize bonding chemistries which do not induce secondary interactions with analytes.

Synthesis of α-CD on Silica (αCD-TEOS-Si) (Method I)

The covalent attachment of β-cyclodextrin to silica can be achieved using a variety of techniques. (Shiraishi et al., Immobilization of b-Cyclodextrin on Silica Gel. Bull. Chem. Soc. Jpn. 1986, 59, 507; Haginaka and J. Wakai, b-Cyclodextrin Bonded Silica for Direct Injection Analysis of Drug Enantiomers in Serum by Liquid Chromatography Anal. Chem. 1990, 62, 997; Tazerouti et al. Enantiomeric Separation of Drugs and Herbicides on a b-Cyclodextrin-Bonded Stationary Phase. Chirality, 2002, 14, 59; Ponchel et al. Cyclodextrin silica-based materials: advanced characterizations and study of their complexing behavior by diffuse reflectance UV-Vis spectroscopy. Microporous and Mesoporous Materials 2004, 75, 261; Belyakova et al., Nanoporous b-Cyclodextrin-Containing Silicas: Synthesis, Structure and Properties. Chemistry, Physics and Technology of Surface. 2014, 5. 386; Guo and W. Qin, Cyclodextrin-Functionalized Silica Nanoparticles with Dendrimer-like Spacers for Enantioselective Capillary Electrochromatography. Electrophoresis 2014, 35, 3549; Ghanem et al., Immobilized β-cyclodextrin-Based Silica vs Polymer Monoliths for Chiral Nano Liquid Chromatographic Separation of Racemates. Talanta 2015, 132, 301.). The direct bonding of α-cyclodextrin to silica can provide many advantages for applications involving lipid removal. Use of rigid and inert silica particles provides phase stability for the α-CD coating and are not soluble in commonly used solvents. In addition, the high stability and rigidity of the support prevents morphological changes of the bonded phase that could decrease performance in SPE cartridge formats during "pass-through" molecular separation methods. Silica gels and particles are widely available and can be utilized in a wide range of pore size, particle size, and surface area allowing for optimization of the α-CD loading conditions as well as processing steps involved in lipid removal. The porosity and high surface area of functionalized nanoporous silica (300-400 $m^2/g$) can also provide a greater concentration of α-cyclodextrin for increased lipid removal. This higher efficiency permits the use of less absorbent per separation and leads to a lower overall expense. By also avoiding the use of aromatic linker groups to bond α-cyclodextrin to silica, thus preventing secondary interactions and retention of analyte, the resulting α-CD bonded silica can display all the desired characteristics outlined above.

A convenient 2-step approach (FIG. 2), involves the use of 3-(triethoxysilyl)propyl isocyanate [(EtO)$_3$Si(CH$_2$)$_3$N=C=O, (TEOS-NCO)] as a linking group to bond α-cyclodextrin to the surface of silica. TEOS-NCO is a triethoxysilane [(EtO)$_3$Si—] which incorporates a short aliphatic propyl chain [—(CH$_2$)$_3$—] and isocyanate group (—N=C=O). When exposed to α-cyclodextrin (a type of cyclic polyol), the isocyanate reacts with one of the hydroxyl groups present on the α-CD linking the two via a carbamate linkage. This reaction results in the formation of a mixture of α-cyclodextrin derivatives incorporating (triethoxysilyl) propyl groups. When the (TEOS)-α-cyclodextrin derivatives are exposed to silica, condensation of these groups at the solid-liquid interface, followed by loss of a molecule of water, results in a covalent bond between the organic and inorganic materials. As this process continues across the surface, a robust siloxane thin-film incorporating α-cyclodextrin is deposited (e.g., covalently linked) throughout the porosity of the silica particle. The deposited (e.g., covalently linked) α-CD monolayer on silica delivers effective retention of lipids with minimal analyte retention in a SPE and dSPE format as is shown in the upcoming sections.

Bonding of α-CD onto Silica: (Method II) Use of Polyisocyanate Linker Groups (α-CD-R—Si)

A second approach (FIG. 3) involves the use of isocyanate linker groups reacted with an aminosilane bonded to the surface of porous silica to generate a reactive isocyanate-functionalized surface capable of direct attachment of α-cyclodextrin. In this approach, an aminosilane is initially bonded to the surface of a porous silica material using silane coupling chemistry. This process occurs due to condensation of the silane with hydroxyl groups (—OH) present on the silica surface and yields a covalently attached organosilane which incorporates a terminal amino group (—NH$_2$). Primary amines react with isocyanate molecules at rates several orders of magnitude faster than those of hydroxyl groups. Consequently, a wide variety of di, tri, or polyisocyante species (e.g., FIG. 4) can be directly bonded to the surface of the functionalized silica under mild conditions in order to activate the material for further attachment of α-cyclodextrin. The final step in this approach involves the reaction of α-cyclodextrin with the isocyanate-functionalized silica (OCN—R-Silica). In this step, elevated temperatures can be used to drive the reaction to completion and achieve high loading of the α-cyclodextrin on the surface and throughout the materials porosity. This final step makes use of the coupling of isocyanate groups with one of the primary hydroxyl groups present on the cyclodextrin to form a carbamate linkage and yield the final α-CD-functionalized silica (α-CD-R-Silica).

Each of these synthetic routes offer a number of advantages for the formation of α-CD-functionalized silica. Method I, which utilizes TEOS-NCO for bonding α-CD to the surface, is a 2-step process which can be performed in a single reactor, simplifying the manufacturing process and lowing overall cost. In addition, the α-CD bonded phase resulting from Method I incorporates a small linker group composed of a short propylene chain and a carbamate linkage. These groups can minimize any undesirable secondary interactions with analyte molecules which can cause their retention in the sorbent bed and lower recovery of these species during analysis. Method II, which utilizes isocyanate linker groups during its procedure, makes use of unfunctionalized α-cyclodextrin on activated silica for the final bonding step. This can result in mono-substituted α-CD pendant groups on the silica surface which can provide a higher affinity for lipid capture. This can result in poly-substituted α-CD pendant groups on the silica surface which can provide a higher affinity for lipid capture. In addition, Method II also results in a longer tether between the bound α-CD and the surface compared to the short propyl group found in Method I. The use of a longer tether will result in increased distance from the silica particle and reduced steric interactions from the surface which could hinder the insertion of large lipid molecules in the α-CD cavity. Also, a wide variety of isocyanate molecules are available (FIG. 4) which provide for synthetic flexibility in forming an α-CD thin-film specifically designed to provide α-cyclodextrin activity towards lipid absorption while minimizing unwanted non-specific interactions of desired target compounds (e.g., analytes).

Column Chromatography

The αCD-TEOS-Si material is also suitable as a column chromatography stationary phase. Tubes were prepared by adding a bottom frit, adding in the respective amount of sorbent, and a top frit was pressed firmly down on top. Typical cartridges used in this evaluation were 1 cc filled with 100 mg of αCD-TEOS-Si. An avocado extract was prepared using the AOAC International QuEChERS official extraction procedure. No SPE solvent conditioning is performed. Next, the ACN extract is diluted 1:1 with water and 1 mL of diluted sample was passed through the cartridge at no more than 1 drop/s, requiring vacuum at 5-8 in. Hg. A green band of concentrating sample matrix (chlorophyll) is visible at the top of the stationary phase bed. Elution was completed by increasing vacuum to 20 in. Hg for 20 s. For LC analysis, the collected eluent can be injected directly onto the system or diluted with mobile phase to match the initial gradient conditions. For GC analysis, the eluent (1 mL) is mixed with 300 mg of anhydrous MgSO$_4$, resulting in phase partitioning of the ACN and water layers. The upper ACN layer is transferred to an autosampler vial for GC-MS analysis. Visual comparison of the untreated ACN extract (before) and the eluent after SPE treatment (after) indicates significant removal of matrix contaminants.

Matrix Removal Evaluation $$\% \text{ Matrix Removal} = \frac{(\text{Extract Peak Area}) - (\text{Sample Peak Area})}{(\text{Extract Peak Area})} \times 100 \quad \text{Equation 1}$$

Matrix removal calculated using chromatographic profile peak areas by GC-MS fullscan analysis.

Figure 6:
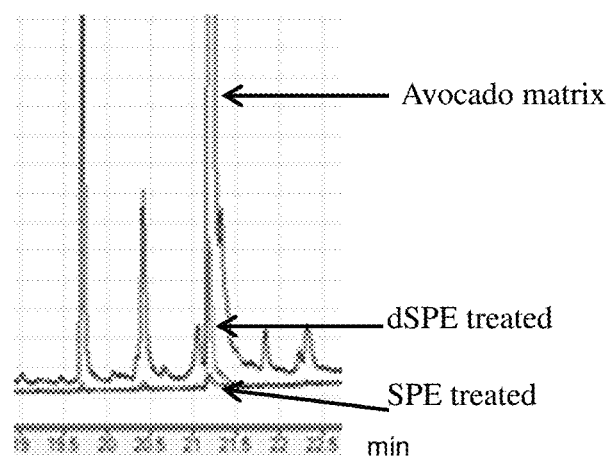
FIG. 6 shows a portion of overlaid chromatograms illustrating the removal of avocado matrix from samples using α-CD-TEOS-Si treatment in SPE format (83.5% matrix removal in total) or dSPE format (79.3% matrix removal total), as analyzed using chromatographic profile peak areas over the whole chromatogram.

For this experiment, GC-MS fullscan was used to determine the amount of matrix removed by comparing the chromatographic profile of an α-CD-TEOS-Si treated extract to the untreated avocado extract. The "Avocado Matrix" chromatographic profile in FIG. 6 was from an untreated avocado extract. The α-CD-TEOS-Si dSPE and αCD-TEOS-Si SPE chromatographic profiles were from samples treated with the αCD-TEOS-Si material in either a dSPE or SPE format, respectively. The peak areas are determined by integrating the entire chromatographic profile and Equation 1 was applied to determine the percentage of matrix removal for each cleanup. The "Extract Peak Area" is the area determined from the untreated extract and the "Sample Peak Area" is determined from the SPE or dSPE treated extracts. Matrix removal was determined to be 79.3% and 83.5% for αCD-TEOS-Si dSPE and αCD-TEOS-Si SPE, respectively.

Applications for Multi-Residue Analysis

Analyte recovery was also determined using the avocado sample from the AOAC QuEChERS extraction and was followed by SPE pass-through cleanup with the αCD-TEOS-Si material. Avocado (15 g) was spiked at 50 ng/mL with a mixture of 14 pesticides: pymetrazine, methamidophos, acephate, omethoate, carbendazim, thiabendazole, dimethoate, imazailil, propoxur, carbaryl, cyprodinil, penconazole, and triphenyl phosphate (TPP) (n=3). The ACN extract is diluted 1:1 with water and 1 mL is loaded and passed through the SPE tube at no more than 1 drop/s. Next, the eluent (0.5 mL) is diluted with water (0.75 mL) to make the solvent composition 8:2, water:ACN for LC-MS/MS analysis (total dilution=5x). For matrix matched calibration standards, blank (unspiked) avocado was taken through the extraction and cleanup protocol and then post spiked at with calibration standards. The recovery values were calculated using Agilent MassHunter software. Recovery and reproducibility values are listed in Tables 7-12.

Protein Precipitation Extraction Protocol and Clean-Up

Biological Samples such as plasma followed a protein precipitation (PPT) workflow as shown in FIG. 8. The samples were spiked as necessary with standards to determine recovery and precision. Phospholipids are the primary co-extractive in plasma and LC-MS/MS was used to monitor matrix removal through a parent ion scan using product ion 184 m/z. First, plasma is mixed with 3 or 4 equivalents of acetonitrile in a centrifuge tube or SPE tube containing a non-drip frit on top of the sorbent. The centrifuge tubes were vortexed, centrifuged, and the supernatant transferred to a SPE tube containing sorbent for clean-up. For non-drip SPE tubes, the plasma/ACN flow was initiated with vacuum or positive pressure and passed through the SPE sorbent bed. Matrix co-extractives are removed by the sorbent and analytes of interest remain in the eluent and are collected in glass tubes. The eluent is diluted with water or evaporated to dryness and reconstituted in mobile phase before injected on the LC-MS/MS.

Sample Clean-Up Method

In this method, the clean-up sorbents included αCD-TEOS-Si, αCD-PMDI-Si and other αCD functionalized silica materials and their blends with C18 on silica as described herein. FIG. 10 shows the cartridge frit stack configuration for use with a workflow using a QuEChERS extract. For cartridges intended for in-situ protein precipitation, a non-drip frit is added. For other applications that do not require solvent retention prior to elution, the non-drip frit is not optional. The extract was generated using the QuEChERS protocol. Next, the extract is mixed with an equal volume of water (50% water). In some experiments, water content was adjusted to only 20% by volume (i.e. (CD-TEOS-Si:C18 blends). Cartridges used in this evaluation were 1 cc to 3 cc containing 30 mg to 100 mg of αCD functionalized silica or blends. The diluted extract is loaded onto the SPE tube containing sorbent. The SPE cartridge is eluted under gravity, or vacuum as required for the non-drip format and the eluent is collected; now enriched with analytes of interest. The eluent is a clear solution cleaned of lipids and other co-extracted matrix components (e.g. chlorophyll). Samples treated with the αCD functionalized silica do not require a drying step prior to LC-MS(/MS) analysis; however, drying with magnesium sulfate is necessary for GC analysis to remove the water added in step B. The final solution is transferred to autosampler vials for LC-MS and/or GC-MS analysis.

Evaluation of Water Content for Matrix Removal and Analyte Recovery

Sorbents that are comprised of neat αCD functionalized silica provide a high water content and a desirable balance of analyte recovery and matrix removal at 50% water content by volume. The size selective nature of the αCD allows trace analytes that do not contain unbranched hydrocarbon chains to remain in solution while the hydrocarbon chains of lipids and other co-extractives enter the αCD cavity and are held by hydrophobic interactions. Decreasing the water content below 50% for neat αCD functionalized silica decreases the amount of co-extractives removed and increasing the water content above 50% increase the interaction strength, but may also non-selectively bind analytes of interest.

Sorbents that are comprised of a blend of αCD and C18 functionalized silica provide for a lower water content to give a desirable balance of analyte recovery and matrix removal. For the subject blends, ~20% water content can provide for efficient removal of co-extractives while analytes of interest remain in solution for subsequent chromatography and detection. Decreasing the water content below 20% decreases the matrix removal while increasing the water content above 20% increases the hydrophobic interaction strength, but can also non-selectively bind analytes of interest. The 20% water content is of interest for use in applications such as PPT and promotes the solubility of hydrophobic target analytes that may become insoluble when water content is increased. Furthermore, lower water content can provide faster evaporation and easier drying of samples with salts.

Synthesis of (TEOS)-α-Cyclodextrin

The major steps involved in the synthesis of αCD-TEOS-Si can be summarized as follows: A) Reaction of α-CD with 3-(triethoxysilyl)propyl isocyanate in DMF (small flask) and the hydrolysis/catalysis of nanoporous silica gel (large flask); B) Heating to 50° C. the reaction of α-CD with 3-(triethoxysilyl)propyl isocyanate; C) Reaction solution containing (TEOS)-α-cyclodextrin derivatives; D) The bonding of (TEOS)-α-cyclodextrin to nanoporous silica at 100° C.; E) Isolation and solvent washing of functionalized silica using centrifugation; F) Soxhlet purification of bonded silica using refluxing methanol; G) Vacuum drying of purified silica product at 50° C.; and H) Final purified product.

Figure 7:
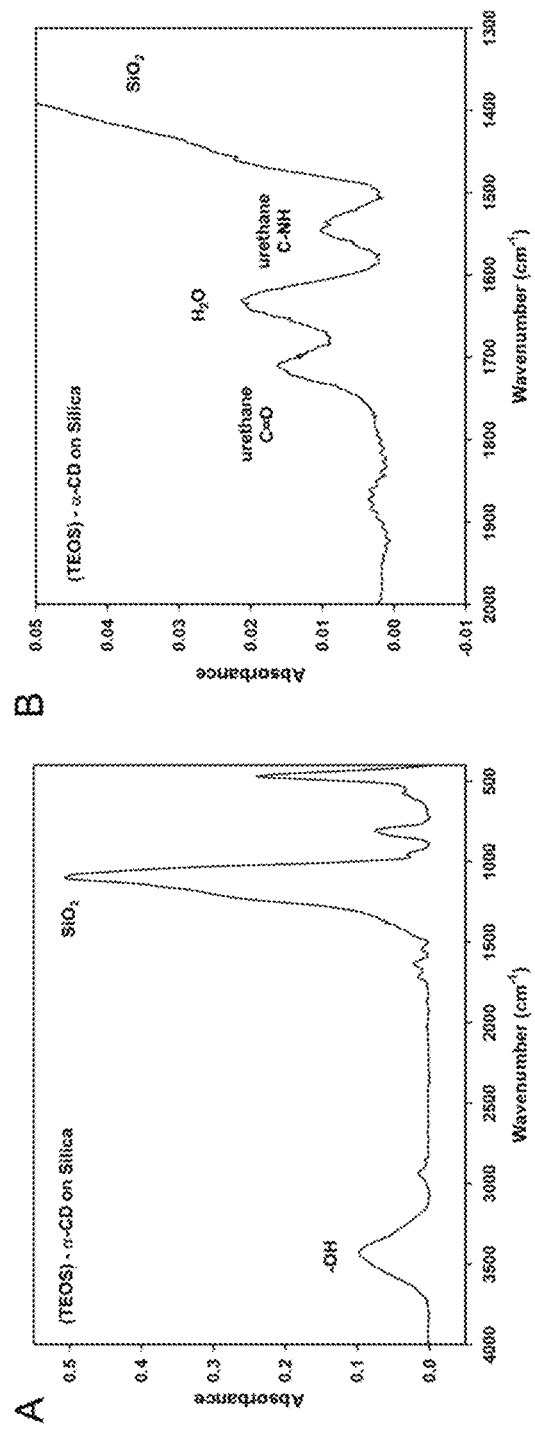
FIG. 7, panels A and B, show FT-IR spectra of nanoporous silica (90 Å) incorporating a bound monolayer of (TEOS)-α-cyclodextrin. Panel A) Complete spectrum and Panel B) spectrum from 1300-2000 $cm^1$. Peaks arising from the α-cyclodextrin are obscured by intense Si—O stretching at 1100 $cm^{-1}$. The bound monolayer is identified from absorbance due to the carbamate-α-CD linkage at 1709 $cm^{-1}$ (urethane C=O) and 1541 $cm^{-1}$ (urethane C—NH).

FIG. 7, panels A and B, show FT-IR spectra of nanoporous silica (90 Å) incorporating a bound monolayer of (TEOS)-α-cyclodextrin. Spectra acquired using KBr pellets under a nitrogen purge. Panel A) Complete spectrum and Panel B) IR spectrum from 1300-2000 cm$^{-1}$. Peaks arising from the α-cyclodextrin are obscured by intense Si—O stretching at 1100 cm$^{-1}$. Identification of the bound monolayer is accomplished using absorbances due to the carbamate-α-CD linkage at 1709 cm$^{-1}$ (urethane C=O) and 1541 cm$^{-1}$ (urethane C—NH).

A thermogravimetric (TGA) analysis was performed of nanoporous silica (90 Å) incorporating a bound monolayer of (TEOS)-α-cyclodextrin. The measured weight loss (not including absorbed $H_2O$) of 22% confirms the observed weight gain experimentally determined before and after the reaction.

A BET surface analysis was performed to show nitrogen desorption curves of 90 Å nanoporous silica and the same silica incorporating a bound monolayer of (TEOS)-α-cyclodextrin. The measured decrease in pore size from 85.7 Å to 62.3 Å suggests the deposition of a thin-film 1.17 nm thick confirming that the deposited film is primarily a monolayer approximately the thickness of one α-cyclodextrin molecule (Table 1).

Scanning electron micrographs images were obtained showing the porous morphology at the surface of 90 Å nanoporous silica incorporating a bound monolayer of (TEOS)-α-cyclodextrin. Images were acquired at A) ×20,000 and B) ×40,000 magnification. No change in morphology is evident compared to unfunctionalized silica supporting the conclusion that the deposited thin-film exists as a monolayer across the entire surface of the material.

Synthesis of (TEOS)-α-Cyclodextrin 25 g of α-cyclodextrin (0.023 mol) was dehydrated under vacuum (1 mbar) at 120° C. for 18 hours. The α-CD was then dissolved in 200 ml of anhydrous DMF with vigorous stirring under an inert atmosphere. Once dissolved, 1 ml of anhydrous triethylamine was added to the solution. After mixing, 5.73 ml of 3-(triethoxysilyl)propyl isocyanate (1 molar equivalent) was added to the solution under vigorous stirring. The flask was then purged with nitrogen gas and sealed under a slight positive pressure of $N_2$. The reaction was then stirred at room temperature for 4 hrs. Afterwards, the temperature was increased to 50° C. and allowed to stir overnight under inert atmosphere.

50 g of porous silica was dispersed in 300 ml of DMF. To this was added 3.5 ml of $NH_4OH/NH_4F$ catalyst solution (see below). This mixture was mechanically stirred at room temperature for several hours at room temperature to promote absorption of the catalyst into the porous silica. Attempted bonding of (TEOS)-α-CD onto silica without use of this catalyst results in low weight loading of the α-CD bonded phase (<10%). The DMF solution incorporating the prepared (TEOS)-α-CD derivatives was then added to the stirring silica/DMF mixture. The flask was purged with $N_2$ then heated to 100° C. and stirred overnight. Total solution volume was ~550 ml. On the next day the silica was collected by vacuum filtration. The silica was then slurry-washed 3× with fresh DMF (600 ml), then 3× with water (1000 ml), and 4× with HOT MeOH (1200 ml). The silica was then dried under vacuum at 45° C. to yield the final material.

$NH_4OH/NH_4F$ catalyst solution consists of: 1.852 g $NH_4F$ dissolved in 100 ml of water. To this was added 20.50 g (22.78 ml) of ammonium hydroxide solution (28-30% in water)

Synthesis of α-CD-PMDI-Si 50 g of porous silica was dehydrated under vacuum (1 mbar) at 120° C. for 18 hours. On the next day, the silica was mixed with 300 ml of anhydrous toluene under a nitrogen atmosphere. Once mixed, 5 ml of anhydrous pyridine was added. Afterwards, 10 ml of (3-aminopropyl)triethoxysilane was added with stirring. Once added, the flask was purged with inert gas and sealed under a slight positive pressure of $N_2$. The reaction was heated to 100° C. and allowed to stir overnight under inert atmosphere. On the next day, the resulting amino-functionalized silica ($NH_2$—Silica) was collected by vacuum filtration. The silica was slurry-washed three times with fresh toluene followed by hot MeOH three times. The silica was then dried under vacuum at 45° C. to yield amino-functionalized silica ($NH_2$—Silica).

20 g of the amino-functionalized silica ($NH_2$—Silica) was placed in a flask and dehydrated under vacuum at 110° C. and 1 mbar for 18 hours. On the next day, the dried silica was mixed with 150 ml of anhydrous DMF under a nitrogen atmosphere. While stirring under a nitrogen atmosphere, 20 ml of Poly(hexamethylene diisocyanate) (PMDI #10 FIG. 4) was added to the mixture. Afterwards, the flask was purged with nitrogen gas and sealed under a slight positive pressure. The reaction was then warmed to 50° C. and allowed to stir overnight under inert atmosphere.

On the following day, the reaction DMF was removed by decanting off the solution. To the resulting isocyanate-functionalized silica (OCN-Silica) was added 20 g of dehydrated α-cyclodextrin dissolved in 200 ml of anhydrous DMF and 2 ml of triethylamine. The resulting mixture was dispersed using overhead mechanical stirring. The reaction flask was purged with nitrogen gas then sealed under a slight positive pressure of $N_2$. The stirring mixture was then heated to 50° C. and stirred for 4 hours. Afterwards, the temperature of the reaction was increased to 100° C. and mechanically stirred overnight under a nitrogen atmosphere. On the next day, the silica was collected by vacuum filtration. The silica was slurry-washed 3× with fresh DMF (600 ml), then 3× with water (1000 ml), and 4× with HOT MeOH (1200 ml). The silica was then dried under vacuum at 45° C. to yield the final αCD-PMDI-Si material. This procedure applies to any possible polyisocyanate monomer, representative examples shown in FIG. 4.

TABLE 3

Bonding results for the deposition of (TEOS)-α-cyclodextrin onto silica materials with increasing pore size.

| Silica pore size (Å) | Silica (g) | α-cyclo-dextrin (g) | Surface Area (m²/g) | Silica Yield (g) | wt. Gain (%) |
|---|---|---|---|---|---|
| 60 | 10.00 | 10.01 | 480 | 11.74 | 17.4 |
| 90 | 10.00 | 10.01 | 401 | 12.63 | 26.1 |
| 90 | 20.00 | 10.01 | 401 | 24.60 | 23.0 |
| 130 | 10.01 | 10.01 | 303 | 12.27 | 22.7 |
| 150 | 10.01 | 10.01 | 289 | 12.35 | 23.4 |
| 200 | 20.17 | 20.17 | 174 | 24.05 | 19.2 |
| 250 | 10.00 | 10.00 | 284 | 12.85 | 28.4 |
| 250 | 20.04 | 10.01 | 284 | 25.27 | 26.1 |
| 300 | 10.03 | 10.02 | 101 | 11.36 | 13.3 |
| 500 | 10.01 | 10.00 | 80 | 10.83 | 8.2 |
| 1000 | 10.00 | 10.00 | 22 | 10.28 | 2.8 |

Figure 11:
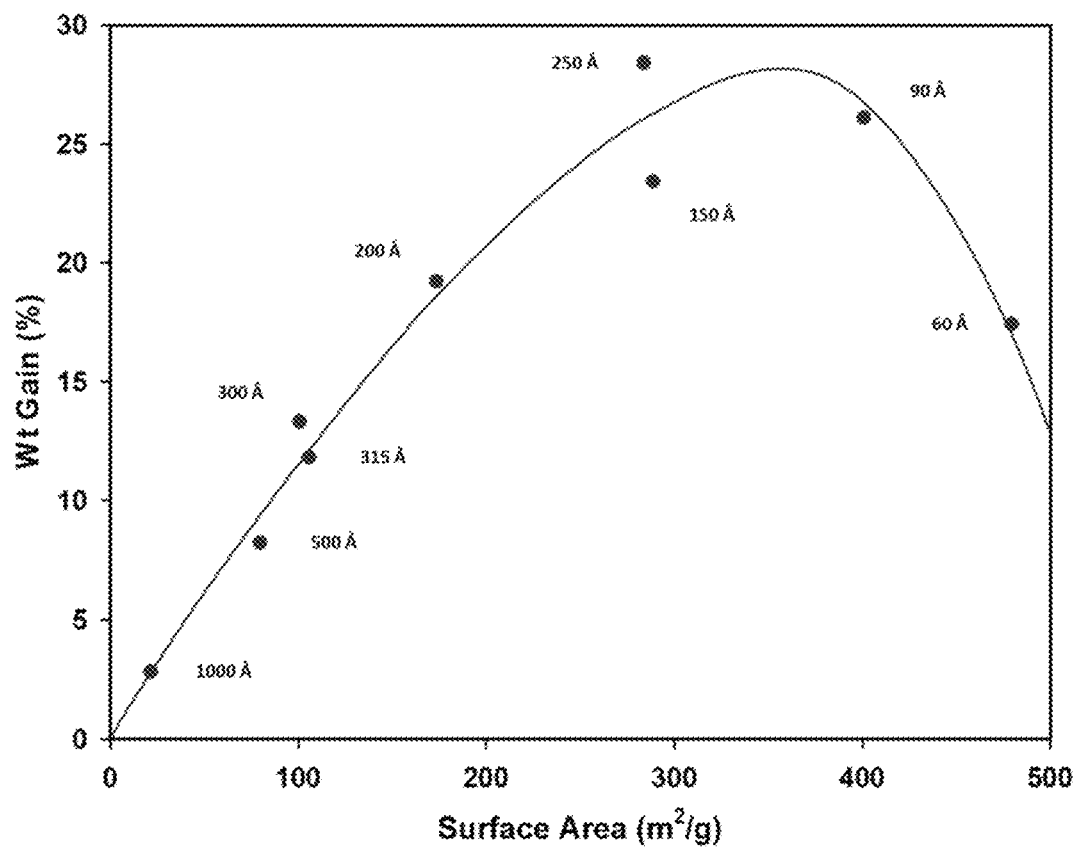
FIG. 11 is a plot showing the observed weight gain of (TEOS)-α-cyclodextrin attached onto various silicas as a function of the materials increasing surface area. The corresponding pore size for each silica is also shown.

FIG. 11 is a plot showing the observed weight grain of (TEOS)-α-cyclodextrin onto various silicas as a function of the materials increasing surface area. The corresponding pore size for each silica is also shown. Weight gain initially increases linearly as a function of surface area but reaches a maximum when using silicas incorporating 100 Å pore size. Decreasing weight gain as pore size drops below 100 Å is likely due to clogging of channels into the silica resulting in incomplete functionalization of the particles interior.

Discussion

The described synthesis of α-CD functionalized silica is simple, inexpensive, and highly effective for generating materials with high α-CD content (e.g., up to >30 wt. %). The α-CD can be chemically deposited on a wide variety of silica materials, such as particles (amorphous or spherical), membranes, monoliths, and other structures. This allows for form factors and applications that can benefit from selective lipid entrapment. In addition, although silica was initially used due to its inertness, wide availability, and low cost, the techniques described here are also amenable to the attachment of cyclodextrin to other substrates consisting of both organic and inorganic materials used for chromatographic separations and/or sample preparation. Any polymeric or inorganic substrate which incorporates either hydroxyl (—OH) or amine (R—NH—R', R—NH$_2$, R—NR'—R") functionality on its surface, or any material which can be chemically modified to introduce these groups on its surface could potentially be utilized with these methods to create a wide variety of α-CD functionalized materials. Examples of additional substrates of interest include, but are not limited to, cellulose, a plentiful and inexpensive natural polysaccharide, which incorporates hydroxyl groups similarly reactive to those found on cyclodextrin, and zirconia (ZrO$_2$) an inorganic oxide and strong Lewis base which incorporates surface hydroxyl groups similar to silica. In addition, many inert polymers such as polyethylene or polypropylene, e.g., which are utilized in filter systems, can be oxidized on their surfaces to introduce hydroxyl functionality which can be adapted for use in the described α-CD functionalization process.

Blending with sorbents containing different functionality can also provide desirable properties with appropriate blending ratios and materials. Sorbents that can be blended with αCD functionalized silica include, but are not limited to, C18, primary secondary amine (PSA), graphitized carbon black (GCB), weak and strong ion exchangers, and weak and strong anion exchangers. C18 on silica produces a blend of interest with αCD functionalized silica for the removal of matrix co-extractives (e.g. lipids) from various sample extracts in an SPE cartridge. The αCD on silica/C18 ratio can be selected based on the αCD and carbon loading. The addition of C18 sorbent provides for the use of lower water content (e.g., 20% versus 50%) which is ideal for protein precipitation (PPT) applications, increased matrix capacity, and improved phospholipid removal (100% versus 54-94%). In some cases, lower water content also improves the solubility of hydrophobic analytes and allows the final eluent to be easily evaporated or dried when necessary (e.g. GC applications).

Supporting Data and Further Experimental Details
I. Materials and Methods A.

TABLE 4

| Abbreviations | |
|---|---|
| αCD | α-Cyclodextrin |
| C18 | Octadecylsilane on silica |
| SPE | Solid Phase Extraction |
| Sorbents | Adsorbent materials used for dSPE |
| QuEChERS | Quick Easy Cheap Effective Rugged Safe extraction protocol |
| PPT | Protein Precipitation |
| ACN | Acetonitrile |
| GCB | Graphitized carbon black |
| PSA | Primary secondary amine on silica |
| dSPE | Dispersive solid phase extraction |

II. Instrumentation and Chemicals

Instruments used were exclusively Agilent Technologies brand and included the following: 7890B GC with 5977 MSD; 1290 LC with 6490 MS/MS (QQQ), and 1290 LC with 6150 MSD.

MS grade solvents were used for eluents and sample preparation reagents. A reverse osmosis water purification system provided purified water for analysis and sample preparation. The αCD and analyte standards were purchased from multiple vendors.

QuEChERS materials including salts and tubes were provided by Agilent Technologies. Agilent Captiva ND and NDL filter tubes were used for protein precipitation analyses. Additional sorbent materials were purchased from multiple vendors.

Polypropylene SPE clean-up tubes were provided by Agilent and assembled in house. The sorbents were retained in the tube using polyethylene, polypropylene, and/or PTFE frits ranging from 3 μm to 15 μm pores.

C18 on silica sorbents were synthesized in-house by Agilent Technologies.

III. Analytical and QC Evaluations and Results a. Matrix Removal Evaluation

A GC-MS fullscan chromatogram overlay of avocado oil was collected before and after treatment with 2:1, αCD-TEOS-Si with integrated profiles for the matrix removal calculation. The profile was manually integrated from 5 min to 29 min across the x-axis at y=0. Matrix removal was determined to be 88.6% in this example.

Equation 1.

The following illustrates a calculation of matrix removal using total peak area of untreated sample extract, purified sample extract, and solvent blank.

$$\% \text{ Matrix Removal} = $$
$$1 - \frac{(\text{Treated Extract Area} - \text{Solvent Blank Area})}{(\text{Untreated Extract Area} - \text{Solvent Blank Area})} \times 100$$
$$88.6\% = 1 - \frac{(78874718 - 60962255)}{(218392355 - 60962255)} \times 100$$

Figure 12:
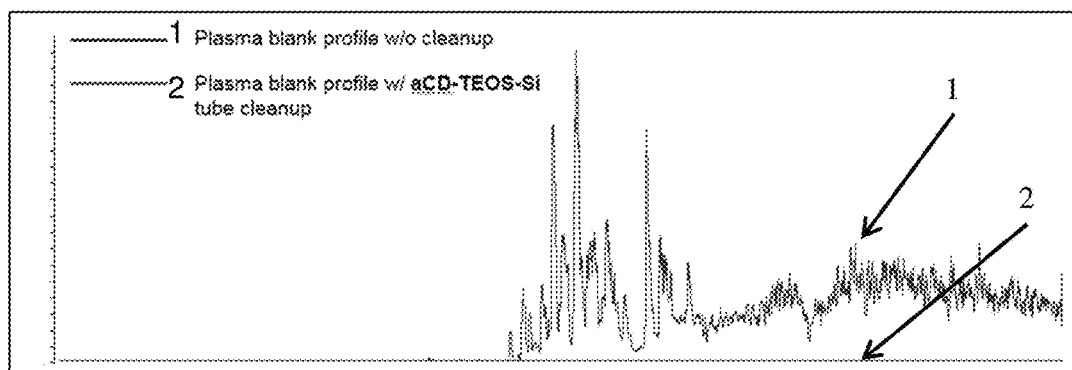
FIG. 12 shows a LC-MS/MS precursor ion scan for 184 m/z parent ion to monitor phospholipids profile for the demonstration of the phospholipids removal in a plasma sample without clean-up and with clean-up using an exemplary α-CD-TEOS-Si modified support.

FIG. 12 shows a LC-MS/MS parent ion scan using 184 m/z for the determination of phospholipid removal using equation 1 and the profile peak area for a plasma sample without clean-up and with clean-up using an α-CD-TEOS-Si modified support. Phospholipid removal was determined to be 100% in this example.

b. Matrix Removal Sorbent Comparisons

TABLE 5

Evaluation of matrix removal with αCD functionalized silica sorbents and blends. All values were determined by GC-MS full scan except for human plasma.

| | Matrix Removal (%) | | | | | |
|---|---|---|---|---|---|---|
| Sample Type | αCD-TEOS-Si | αCD-PMDI-Si | αCD-HMDI-Si | αCD-TEOS-Si/C18, 2:1 blend | αCD-PMDI-Si/C18, 2:1 blend | αCD-HMDI-Si/C18, 2:1 blend |
| Avocado | 72 | 70 | 59 | 70 | NA | NA |
| Avocado Oil | 60 | 91 | 67 | 88 | 70 | 60 |
| Olive Oil | 70 | 92 | 65 | 87 | NA | NA |
| Infant Formula | 75 | 94 | 81 | 96 | 80 | 87 |
| Beef Liver | 53 | 71 | 80 | 83 | 76 | 72 |
| Human Plasma* | 97 | 55 | 58 | 100 | 100 | 100 |

*Evaluated using protocol E followed by LC-MS/MS product ion scan, 184 m/z for phospholipids detection.

TABLE 6

Matrix removal and material property comparison of αCD functionalized silica on different base silica particles based on αCD-TEOS-Si using method I.

| Particle property | αCD-TEOS-Si Material | | | | |
|---|---|---|---|---|---|
| | Batch A | Batch B | Batch C | Batch D | Batch E |
| Pore Size (Å) | 500 | 150 | 200 | 250 | 90 |
| Particle Size (μm) | 50-100 | 35-70 | 20 | 15-20 | 63-200 |
| Surface Area (m$^2$/g) | 80 | 289 | 174 | 284 | 400 |
| αCD Loading (%) | 8 | 19 | 19 | 26 | 30 |
| Type | Amorphous | Amorphous | Spherical | Amorphous | Amorphous |
| Sample Type | Matrix Removal (%) | | | | |
| Avocado | 67 | 68 | 57 | 72 | 68 |
| Avocado Oil | 45 | 50 | 54 | 60 | 57 |
| Olive Oil | 30 | 45 | 56 | 70 | 58 |
| Infant Formula | 50 | 56 | 60 | 75 | 55 |
| Beef Liver | 43 | 44 | 30 | 53 | 50 |
| Human Plasma | 87 | 96 | 95 | 97 | 54 |

TABLE 7

Matrix removal comparison of different αCD functionalized silica materials and their respective blends with C18.

| Matrix | Matrix Removal (%) | | | | | |
|---|---|---|---|---|---|---|
| | aCD-TEOS-Si | aCD-PMDI-Si | aCD-HMDI-Si | aCD-TEOS-Si/C18, 2:1 | aCD-PMDI-Si/C18, 2:1 | aCD-HMDI-Si/C18, 2:1 |
| AV oil | 60 | 91 | 67 | 88 | 71 | 60 |
| Beef Kidney | 52 | 74 | 45 | 73 | 72 | NA |
| Human plasma* | 97 | 55 | 58 | 100 | 100 | 100 |

*Evaluated using protocol E followed by LC-MS/MS product ion scan, 184 m/z for phospholipids detection.

c. Calculation of Analyte Recoveries

Instrumental analysis methods were optimized for the various analyses using LC-MS/MS, GC-MS, and GC-MS/MS to achieve the selectivity, sensitivity, and broad detection necessary for applications including multi-class, multi-residue pesticide, veterinary drug analysis, pharmaceuticals, and drugs of abuse. Appropriate ions were selected for the various analytes as primary, secondary, and tertiary transitions for quantitation and confirmation. Chromatographic peaks corresponding to the analytes of interest were integrated to give peak areas and compared to solvent standard and/or matrix matched calibration curves using Mass Hunter and Chem Station software to give calculated peak area, final concentration, percent recovery, and percent relative standard deviation. Additionally, single point calibration was implemented to calculate percent recovery by using the sample and standard peak areas in the formula below.

$$\text{Recovery (\%)} = \frac{\text{Peak Area of Sample}}{\text{Peak Area of Standard}} \times 100$$

Equation 2.

Percent recovery calculation for single point calibration used in this study. Calibrators and sample pre-spikes were prepared in n=3-6.

d. Recovery and Reproducibility Results for Practical Applications

TABLE 8

Recovery and precision for pesticides in avocado oil by LC-MS/MS. Samples were spiked with pesticides at 50 ng/g and taken through the sample preparation procedure. Blank samples were taken through the entire sample preparation process and post-spiked for matrix match calibration standards. Precision was determined using replicates of 6.

| | αCD-TEOS-Si | | αCD-TEOS-Si/C18, 2:1 | | αCD-PMDI-Si | |
|---|---|---|---|---|---|---|
| Analyte | % Rec | % RSD | % Rec | % RSD | % Rec | % RSD |
| Pymetrazine | 100.2 | 1.9 | 99.5 | 2.0 | 104.6 | 5.5 |
| Methamidophos | 104.7 | 2.4 | 99.4 | 1.1 | 108.9 | 4.6 |
| Acephate | 106.9 | 4.7 | 104.1 | 2.6 | 109.8 | 2.9 |
| Omethoate | 100.4 | 2.2 | 100.5 | 0.3 | 102.4 | 2.7 |
| Carbendazim | 102.3 | 3.3 | 100.9 | 1.6 | 109.0 | 1.7 |
| Thiabendazole | 99.7 | 1.9 | 99.6 | 2.2 | 109.2 | 3.3 |
| Imidacloprid | 102.2 | 2.7 | 95.9 | 2.3 | 111.2 | 2.0 |
| Dimethoate | 105.6 | 3.4 | 108.7 | 3.1 | 112.5 | 3.9 |
| Imazalil | 96.4 | 1.8 | 76.5 | 1.5 | 115.2 | 2.3 |
| Propoxur | 107.0 | 4.2 | 105.8 | 3.5 | 109.8 | 3.8 |
| Cyprodinil | 107.0 | 1.6 | 80.5 | 1.6 | 103.9 | 1.7 |
| Carbaryl | 126.3 | 3.9 | 128.2 | 5.1 | 101.3 | 3.0 |
| Penconazole | 103.2 | 2.6 | 85.9 | 1.0 | 106.6 | 4.3 |
| TPP | 109.5 | 2.9 | 100.1 | 2.3 | 105.1 | 5.6 |

TABLE 9

Recovery and precision for pesticides in avocado oil by GC-MS/MS. Samples were spiked with pesticides at 20 ng/g and taken through the sample preparation procedure. Blank samples were taken through the entire sample preparation process and post-spiked for matrix match calibration standards. Precision was determined using replicates of 6.

| | αCD-TEOS-Si | | αCD-TEOS-Si/C18, 2:1 | |
|---|---|---|---|---|
| Analyte | % Rec | % RSD | % Rec | % RSD |
| Dichlorvos | 106 | 9.6 | 120 | 13.4 |
| 2-Phenylphenol | 108 | 11.6 | 108 | 12.2 |
| Ethalfluralin | 102 | 3.2 | 114 | 13.4 |
| Sulfotep | 107 | 1.8 | 103 | 11.5 |
| Atrazin | 105 | 2.0 | 111 | 8.7 |
| Lindane | 107 | 1.2 | 105 | 12.2 |
| Chlorothalonil | 106 | 2.9 | 109 | 13.1 |
| Diazinon | 107 | 1.9 | 95 | 10.4 |
| Chlorpyriphos-Me | 102 | 0.5 | 93 | 7.8 |
| Dichlorfluanid | 110 | 1.3 | 118 | 12.4 |
| Aldrin | 63 | 3.0 | 55 | 16.9 |
| Tolylfluanid | 105 | 2.1 | 111 | 15.7 |
| Procymidone | 106 | 2.1 | 105 | 13.2 |
| Bupirimate | 103 | 2.5 | 103 | 8.7 |
| Endrin | 93 | 2.0 | 87 | 12.2 |
| Endosulfan sulfate | 107 | 1.2 | 97 | 16.3 |
| DDT | 67 | 3.5 | 71 | 15.8 |
| Iprodione | 89 | 2.9 | 106 | 15.0 |
| Coumaphos | 107 | 2.5 | 103 | 16.7 |
| Permethrin | 74 | 3.8 | 62 | 16.5 |
| Deltamethrin | 79 | 3.0 | 74 | 18.8 |

TABLE 10

Recovery and precision for hydrophobic pesticides in avocado oil by GC-MS/MS. Samples were spiked with pesticides at 20 ng/g and taken through the sample preparation procedure. Blank samples were taken through the entire sample preparation process and post-spiked for matrix match calibration standards. Precision was determined using replicates of 6.

| Analyte | aCD-TEOS-Si | aCD-PMDI-Si | aCD-HMDI-Si | aCD-TEOS-Si/C18, 2:1 | aCD-PMDI-Si/C18, 2:1 | aCD-HMDI-Si/C18, 2:1 |
|---|---|---|---|---|---|---|
| Aldrin | 63 | 12 | 52 | 55 | 43 | 52 |
| Endrin | 93 | 30 | 80 | 87 | 69 | 81 |
| DDT | 67 | 5 | 52 | 71 | 50 | 65 |
| Permethrin | 74 | 17 | 63 | 62 | 49 | 61 |
| Deltamethrin | 79 | 9 | 67 | 74 | 55 | 70 |

TABLE 11

Recovery and precision for drugs in human plasma by LC-MS/MS. Samples were spiked with drugs at 1 ng/mL and taken through the sample preparation procedure. Blank samples were taken through the entire sample preparation process and post-spiked for matrix match calibration standards. Precision was determined using replicates of 6.

| | αCD-TEOS-Si | | αCD-TEOS-Si/C18, 2:1 | |
|---|---|---|---|---|
| Analyte | % Rec | % RSD | % Rec | % RSD |
| 5-Fluorouracil | 97 | 10.5 | 87 | 10.2 |
| Gemcitabine | 86 | 7.1 | 83 | 3.3 |
| Amphetamine-D5 | 73 | 4.3 | 86 | 7.5 |
| Amphetamine | 75 | 5.2 | 84 | 8.0 |
| Metoprolol | 89 | 0.9 | 104 | 6.9 |
| Prednisone | 81 | 1.9 | 84 | 0.9 |
| Hydrocortisone | 87 | 2.0 | 102 | 1.7 |
| Amitriptyline-D3 | 94 | 5.9 | 74 | 16.5 |
| Amitriptyline | 98 | 5.1 | 75 | 16.8 |
| Warfarin | 75 | 13.5 | 93 | 3.0 |
| Androstenedione | 80 | 7.0 | 86 | 2.7 |
| Hydroxyprogesterone | 88 | 6.5 | 93 | 9.4 |
| Atorvastatin | 69 | 16.6 | 107 | 13.4 |
| Diclofenac | 104 | 9.2 | 113 | 13.7 |
| Progesterone-D9 | 78 | 15.9 | 84 | 7.2 |

TABLE 12

Recovery and precision for veterinary drugs in beef liver by LC-MS/MS. Samples were spiked with drugs at 50 ng/g and taken through the sample preparation procedure. Blank samples were taken through the entire sample preparation process and post-spiked for matrix match calibration standards. Precision was determined using replicates of 6.

| | αCD-TEOS-Si | | αCD-TEOS-Si/C18, 2:1 | |
|---|---|---|---|---|
| Analyte | % Rec | % RSD | % Rec | % RSD |
| Amoxicillin | 108 | 2.9 | 103 | 4.8 |
| Metronidazole—OH | 108 | 3.9 | 101 | 1.7 |
| Lincomycin | 107 | 4.2 | 105 | 4.4 |
| Levamisole | 113 | 8.2 | 111 | 5.4 |
| Ampicilin | 109 | 6.5 | 96 | 5.6 |
| Norfloxacin | 104 | 11.6 | 105 | 3.5 |
| Ciprofloxacin | 103 | 10.9 | 103 | 5.0 |
| Oxytetracycline | 101 | 7.6 | 99 | 7.4 |
| Penicillin G-d7 | 95 | 16.5 | 46 | 6.6 |
| Danofloxacin | 96 | 9.6 | 110 | 4.5 |
| Ractopamine | 109 | 2.9 | 104 | 7.9 |
| Doxycycline | 99 | 5.8 | 102 | 6.3 |
| Tetracycline | 101 | 7.8 | 101 | 5.7 |
| Cefazolin | 110 | 13.9 | 109 | 9.4 |
| Sulfamethizole | 103 | 6.4 | 101 | 3.4 |
| Sulfamethoxypyridazine | 108 | 7.5 | 101 | 13.1 |
| Demeclocycline | 92 | 17.2 | 90 | 9.0 |
| Difloxacin | 98 | 8.2 | 102 | 6.3 |
| Morantel | 109 | 15.8 | 105 | 3.1 |
| Gamithromycin | 118 | 15.2 | 102 | 7.4 |
| Chlortetracycline | 99 | 19.0 | 97 | 8.5 |
| Florfenicol | 103 | 8.7 | 101 | 11.1 |
| Chloramphenicol | 106 | 7.3 | 102 | 3.7 |
| Clorsulon | 110 | 13.7 | 92 | 9.0 |
| Tylosin | 104 | 5.3 | 100 | 5.8 |
| Prednisone | 108 | 10.0 | 100 | 10.5 |
| Penicillin V | 109 | 7.4 | 101 | 14.6 |
| Fenbendazole | 120 | 20.3 | 95 | 8.6 |
| Oxacillin | 107 | 6.4 | 104 | 8.7 |
| Cloxacillin | 112 | 8.2 | 101 | 8.0 |
| Nafcillin | 105 | 7.5 | 113 | 14.6 |
| Ketoprofen | 107 | 10.3 | 88 | 14.4 |
| Fluixin-D3 | 106 | 5.6 | 94 | 11.9 |
| Melengestrol acetate | 106 | 4.4 | 60 | 18.8 |
| Niclosamide | 111 | 16.9 | 85 | 14.5 |

IV. Analytical Protocols

SPE Tube Composition

Tubes were 1 to 3 cc and contained 2 to 3 frits. The tube consists of a bottom frit, 30 to 100 mg of sorbent and a top frit to contain the sorbent. In non-drip formats, a hydrophobic frit is placed below the top frit to hold solvent until vacuum is pulled.

Extraction Protocol A (QuEChERS—Avocado)

A thoroughly homogenized avocado sample was weighed (15 g) into a 50 mL centrifuge tube and spiked with appropriate internal and QC standards as required. An un-spiked sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then transferred to the clean-up step A or B.

Extraction Protocol B (QuEChERS—Tissue)

A thoroughly homogenized tissue sample was weighed (2 g) into a 50 mL centrifuge tube and spiked with appropriate internal and QC standards as required. An un-spiked beef liver sample was also carried through the extraction process, to be used later as a matrix blank for matrix matched calibration standards. To the sample, 8 mL of 30 mM $KH_2PO_4$, pH 7.0 was added, followed by vortexing for 10 s. Then 10 mL acetonitrile containing 5% formic acid was added to the tube and mixed for 2 min using a mechanical shaking unit. A salt packet containing anhydrous 1 g sodium chloride, 1 g sodium citrate, 0.5 g disodium citrate sequihydrate, and 4.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then transferred to the clean-up step A or B.

Extraction Protocol C—(QuEChERS—Oils)

A thoroughly homogenized avocado sample was weighed (3 g) into a 50 mL centrifuge tube and spiked with appropriate internal and QC standards. Then 12 mL of reagent water was added and thoroughly mixed with the oil. An un-spiked sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the mixture, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then transferred to the clean-up step A or B.

Extraction Protocol D—(QuEChERS—Liquids)

A liquid sample was weighed (15 g) into a 50 mL centrifuge tube and spiked with appropriate internal and QC standards as required. An unspiked sample was also carried through the extraction process, to be used later as a matrix blank for matrix matched calibration standards. Then 15 mL acetonitrile containing 1% acetic acid was added to the tube and mixed for 2 min using a mechanical shaking unit. A salt packet containing anhydrous 1.5 g sodium acetate and 6.0 g magnesium sulfate was poured into the slurry, the tube capped, and quickly shaken to avoid salt clumps. The sample was placed on the shaking unit again for 2 min. The tube was then placed in a centrifuge and spun at 5000 rpm for 5 min. The resulting supernatant gave phase separation of the upper, acetonitrile layer which was then transferred to the clean-up step A or B.

Extraction Protocol E—(PPT—Plasma)

Add 0.06 to 2 mL acetonitrile to a 2 mL centrifuge tube or non-drip SPE tube. Add 0.02 mL to 0.400 mL plasma into the ACN to precipitate proteins. For centrifuge PPT, centrifuge at 12000 rpm for 3 min and transfer to cleanup step C. For in-tube PPT, pull vacuum to initiate flow through clean-up sorbent.

Cleanup A (50% Water)

The acetonitrile extract is mixed with an equivalent volume of reagent water (e.g. 0.5 mL acetonitrile extract; 0.5 mL reagent water) and transferred to an SPE clean-up tube. Eluent was allowed to drip through the SPE tube under gravity into a glass collection tube. After gravity flow stopped, vacuum was pulled to complete the transfer. For LC analysis, the eluent was diluted with additional water as required and transferred to an autosampler vial for analysis. For GC analysis, the eluent was transferred to a 2 mL centrifuge tube. Magnesium sulfate portion-wise was added until no water was observed in the tube. The upper ACN layer was then transferred to an auto-sampler vial for GC analysis.

Cleanup (SPE) B (20% Water)

The acetonitrile extract is mixed 4:1 with reagent water (e.g. 0.5 mL acetonitrile extract; 0.15 mL reagent water) and transferred to an SPE clean-up tube. Eluent was allowed to drip through the SPE tube under gravity into a glass collection tube. After gravity flow stopped, vacuum was pulled to complete the transfer. For LC analysis, the eluent was diluted with additional water as required and transferred to an autosampler vial for analysis. For GC analysis, the eluent was transferred to a 2 mL centrifuge tube. Magnesium sulfate portion-wise was added until no water was observed in the tube. The upper ACN layer was then transferred to an auto-sampler vial for GC analysis.

Cleanup (SPE) C (PPT)

The ACN/plasma mixture was transferred to an SPE clean-up tube or vacuum was initiated in the non-drip format. Eluent was pulled through the SPE tube into a glass collection tube. Vacuum was then increased to complete the transfer. For LC analysis, the eluent was diluted with additional water as required or evaporated to dryness and then reconstituted with mobile phase. The solution was then transferred to an auto-sampler vial for LC analysis.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

What is claimed is:

1. A solid phase sorbent for preparation of analytical samples, comprising particles that are surface modified with an α-cyclodextrin moiety, wherein the α-cyclodextrin moiety is covalently linked to the surface of the particles via a carbamate, a thiocarbamate, an ester, an amide, a thioamide, or a keto linking group, and the α-cyclodextrin moiety is α-cyclodextrin or a modified α-cyclodextrin, wherein at least one glucose subunit of the modified α-cyclodextrin is modified with an alkyl, an acyl, an amine, a thiol, an aldehyde, a ketone, an azide, a carboxylic acid, an active ester, or an isothiocyanate group.

2. The solid phase sorbent of claim 1, wherein the particles comprise the formula:

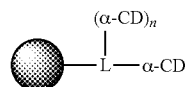

wherein:
L is a linker;
α-CD is the α-cyclodextrin moiety and
n is 0, or an integer from 1 to 6.

3. The solid phase sorbent of claim 1, wherein the α-cyclodextrin moiety is a modified α-cyclodextrin that includes a specific binding moiety, a water soluble group, or a detectable moiety.

4. A solid phase sorbent for preparation of analytical samples, comprising particles that are surface modified with an α-cyclodextrin moiety, wherein the particles comprise the formula:

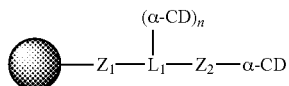

wherein:
$L_1$ is a linker;
$Z_1$ is a linking functional group selected from carbamate, thiocarbamate, ester, amide, thioamide, and keto;
$Z_2$ is a linking functional group selected from carbamate, thiocarbamate, ester, amide, thioamide, urea, thiourea, amino, keto and ether;
α-CD is the α-cyclodextrin moiety, wherein the α-cyclodextrin moiety is α-cyclodextrin or a modified α-cyclodextrin, wherein at least one glucose subunit of the modified α-cyclodextrin is modified with an alkyl, an acyl, an amine, a thiol, an aldehyde, a ketone, an azide, a carboxylic acid, an active ester, or an isothiocyanate group and
n is 0, or an integer from 1 to 6.

5. The solid phase sorbent of claim 4, wherein:
the particles are silica particles;
$Z^1$ is independently selected from —N(R')C(=O)—, —N(R')C(=O)O—, —N(R')C(=S)—, —N(R')C(=S)O—, —CO—, and —CO$_2$—, and $Z^2$ is independently selected from —N(R')C(=O)—, —N(R')C(=O)O—, —N(R')C(=S)—, —N(R')C(=S)O—, —N(R')C(=O)N(R')—, —N(R')C(=S)N(R')—, —CO—, —CO$_2$—, —NR'—, and —O— wherein each R' is independently H, a lower alkyl or a substituted lower alkyl;
$L_1$ is a $C_1$-$C_{20}$ alkyl, $C_1$-$C_{20}$ substituted alkyl, $C_1$-$C_{20}$ aryl, $C_1$-$C_{20}$ substituted aryl, $C_1$-$C_{20}$ heteroaryl, $C_1$-$C_{20}$ substituted heteroaryl or a PEG linking group; and
α-CD is the α-cyclodextrin moiety.

6. The solid phase sorbent of claim 4, wherein the particles comprise the formula:

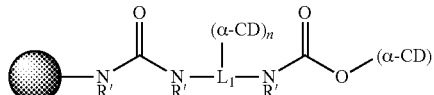

wherein each R' is independently H, alkyl or substituted alkyl.

7. The solid phase sorbent of claim 4, wherein $L_1$ is selected from:

a) —(CH$_2$)$_m$— where m is an integer from 2 to 12;

b)

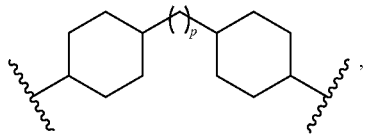

wherein p is 0 or an integer from 1 to 6;

c)

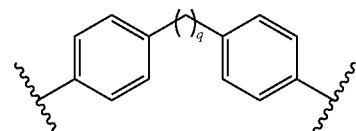

wherein q is 0 or an integer from 1 to 6;

d)

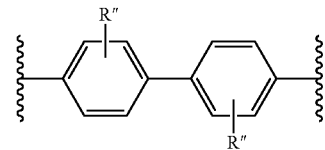

wherein each R" is an optional substituent;

e)

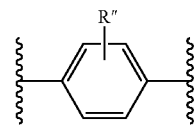

wherein R" is an optional substituent; and f)

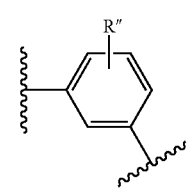

wherein R'' is an optional substituent; and
g)

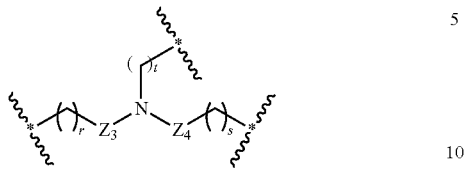

wherein r, s and t are independently an integer from 2 to 12.

8. The solid phase sorbent of claim 1, wherein the linked α-cyclodextrin moiety has the structure:

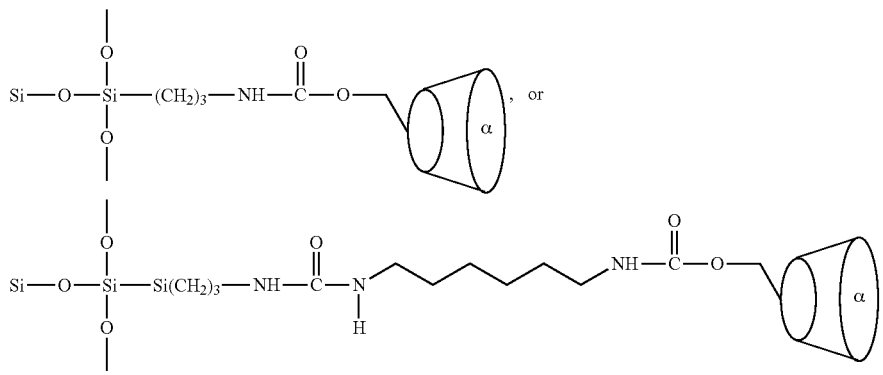

9. The solid phase sorbent of claim 1, wherein the particles are surface modified with a thin film of the α-cyclodextrin moiety.

10. The solid phase sorbent of claim 9, wherein the thin film comprises a monolayer of the α-cyclodextrin moiety attached to the surface of a particle.

11. A method of reducing matrix effects in an analytical sample, the method comprising:
contacting a sample comprising a matrix-interfering agent and an analyte with the solid phase sorbent of claim 1 to produce a contacted sample wherein the matrix-interfering agent binds to the α-cyclodextrin modified particles;
separating the α-cyclodextrin modified particles from the contacted sample to produce a matrix-reduced composition; and
detecting the analyte in the matrix-reduced composition.

12. The method of claim 11, wherein the matrix-reduced composition has a reduced deleterious effect on sensitivity of the detecting the analyte.

13. The method of claim 11, further comprising quantitating the amount of analyte in the sample, wherein the matrix-reduced composition has reduced matrix effects on the quantitating the amount of analyte.

14. The method of claim 11, wherein the matrix interfering agent is an aliphatic lipid and the support binds the aliphatic lipid via a lipid-α-cyclodextrin complex.

15. A system for analytical sample treatment, comprising:
a container having a fluid inlet and a fluid outlet;
a solid phase sorbent according to claim 1 disposed in the container.

16. The system of claim 15, further comprising a non-drip frit operably connected to the solid phase sorbent that is disposed in the container between the solid phase sorbent and the fluid inlet.

17. The solid phase sorbent of claim 4, wherein the α-cyclodextrin moiety is α-cyclodextrin.

18. The solid phase sorbent of claim 1, wherein the α-cyclodextrin moiety is α-cyclodextrin, methyl-α-cyclodextrin, or (2-hydroxypropyl)-α-cyclodextrin.

19. The solid phase sorbent of claim 1, wherein the α-cyclodextrin moiety is α-cyclodextrin.

20. The method of claim 14, where in the method further comprises eluting the aliphatic lipid from the support.

* * * * *

UNITED STATES PATENT AND TRADEMARK OFFICE
CERTIFICATE OF CORRECTION

PATENT NO. : 10,436,684 B2
APPLICATION NO. : 15/269647
DATED : October 8, 2019
INVENTOR(S) : Bruce Richter et al.

It is certified that error appears in the above-identified patent and that said Letters Patent is hereby corrected as shown below:

In the Specification

Column 1, Line 39, delete "phenoxyalcanoic" and insert -- phenoxyalkanoic --, therefor.

Column 4, Line 26, delete "10-1" and insert -- 10-11 --, therefor.

Column 4, Line 32, delete "lx" and insert -- 1× --, therefor.

Column 7, Line 2, delete "(N—O)," and insert -- (N→O), --, therefor.

Column 10, Line 57, delete "propyltriethyoxysilane" and insert -- propyltriethoxysilane --, therefor.

Column 15, Line 27, delete "α-cyclodextrin_co-polymer" and insert -- α-cyclodextrin co-polymer --, therefor.

Column 15, Line 32, delete "α-cyclodextrin_co-monomer." and insert -- α-cyclodextrin co-monomer. --, therefor.

Column 16, Line 14, delete "can can" and insert -- can --, therefor.

Column 17, Line 50, delete "polymethacylate, polypyrole," and insert -- polymethacrylate, polypyrrole, --, therefor.

Column 18, Line 44, delete "isothiocyanante" and insert -- isothiocyanate --, therefor.

Column 20, Line 6, delete "6-hyhroxyl," and insert -- 6-hydroxyl, --, therefor.

Column 20, Line 11, delete "6-hyhroxyl," and insert -- 6-hydroxyl, --, therefor.

Column 25, Line 7, after "can" insert -- be --.

Signed and Sealed this
Fourteenth Day of July, 2020

Andrei Iancu
*Director of the United States Patent and Trademark Office*

CERTIFICATE OF CORRECTION (continued)

Column 26, Line 15, delete "lysophsosplipids," and insert -- lysophospholipids, --, therefor.

Column 35, Line 37, delete "polyisocyante" and insert -- polyisocyanate --, therefor.

Column 37, Line 6, delete "pymetrazine," and insert -- pymetrozine, --, therefor.

Column 37, Line 8, delete "imazailil," and insert -- imazalil, --, therefor.

Column 37, Line 53, delete "(CD-" and insert -- (αCD- --, therefor.

Column 37, Line 63, delete "LC-MS(/MS)" and insert -- LC-MS/MS --, therefor.

Column 39, Line 47, after "water)" insert -- . --.

Column 40, Line 44, delete "grain" and insert -- gain --, therefor.

Column 44, Line 20, delete "Pymetrazine" and insert -- Pymetrozine --, therefor.

Column 44, Line 53, delete "Atrazin" and insert -- Atrazine --, therefor.

Column 44, Line 57, delete "Dichlorfluanid" and insert -- Dichlofluanid --, therefor.

Column 45, Line 65, delete "Ampicilin" and insert -- Ampicillin --, therefor.

Column 46, Line 36, delete "Fluixin-D3" and insert -- Flunixin-D3 --, therefor.

Column 47, Lines 8-9, delete "sequihydrate," and insert -- sesquihydrate, --, therefor.

In the Claims

Column 50, Lines 11-18, Claim 7, delete " 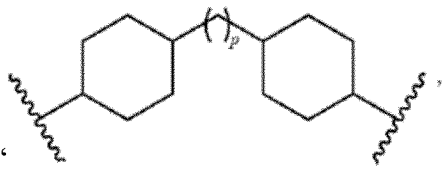 " and insert -- 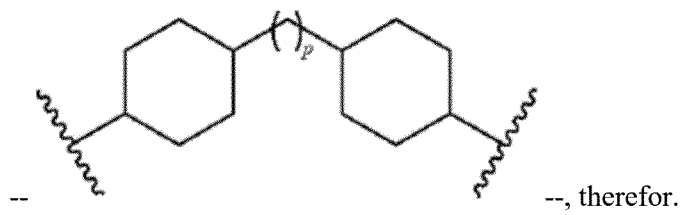 --, therefor.

Column 52, Line 47, Claim 17, delete "claim 4," and insert -- claim 6, --, therefor.

Column 52, Line 54, Claim 20, delete "where in" and insert -- wherein --, therefor.